(12) United States Patent
Makino et al.

(10) Patent No.: US 10,894,973 B2
(45) Date of Patent: Jan. 19, 2021

(54) NUCLEIC ACID INTRODUCTION METHOD, NUCLEIC ACID DETECTION METHOD, BIOMOLECULE ANALYSIS METHOD, ARRAY DEVICE FOR BIOMOLECULE QUANTIFICATION, AND BIOMOLECULE ANALYSIS KIT

(71) Applicant: TOPPAN PRINTING CO., LTD., Taito-ku (JP)

(72) Inventors: Yoichi Makino, Taito-ku (JP); Tomoyuki Ozawa, Taito-ku (JP); Shuichi Akashi, Taito-ku (JP); Tomoko Kunitomi, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/586,622

(22) Filed: May 4, 2017

(65) Prior Publication Data

US 2017/0233790 A1 Aug. 17, 2017

Related U.S. Application Data

(63) Continuation of application No. PCT/JP2015/081029, filed on Nov. 4, 2015.

(30) Foreign Application Priority Data

Nov. 4, 2014 (JP) .................................. 2014-224639
Feb. 6, 2015 (JP) .................................. 2015-022624

(51) Int. Cl.
*C12Q 1/68* (2018.01)
*C12Q 1/682* (2018.01)
(Continued)

(52) U.S. Cl.
CPC .......... *C12Q 1/682* (2013.01); *B01L 3/50853* (2013.01); *C12M 33/00* (2013.01);
(Continued)

(58) Field of Classification Search
CPC ......... B01L 2300/04; B01L 2300/0829; B01L 2300/168; B01L 3/50853; C12M 33/00;
(Continued)

(56) References Cited

U.S. PATENT DOCUMENTS 6,440,706 B1 8/2002 Vogelstein et al.
6,753,147 B2 6/2004 Vogelstein et al.
(Continued)

FOREIGN PATENT DOCUMENTS

CN 101896275 A 11/2010
CN 102409039 A 4/2012
(Continued)

OTHER PUBLICATIONS

ResinLab.com "cyanoacrylate adhesives" (Year: 2018).*
(Continued)

*Primary Examiner* — Betty J Forman
(74) *Attorney, Agent, or Firm* — Oblon, McClelland, Maier & Neustadt, L.L.P.

(57) ABSTRACT

An array device including a base having wells, a cover positioned over the base with a gap from the base such that openings of the wells are covered by the cover with the gap in between, an injection port communicating with the gap, a discharge port communicating with the gap and positioned apart from the injection port, and a waste liquid vessel which collects liquid that flows from the gap via the discharge port and is positioned at a level different from the gap forming a channel. The discharge port is placed to discharge a surplus
(Continued)

aqueous solution outside the wells from the discharge port by an oleaginous sealing liquid to be delivered from the injection port.

11 Claims, 21 Drawing Sheets

(51) Int. Cl.

| | | |
|---|---|---|
| *G01N 33/53* | (2006.01) | |
| *C12M 1/42* | (2006.01) | |
| *C12M 1/26* | (2006.01) | |
| *B01L 3/00* | (2006.01) | |
| *C12Q 1/6825* | (2018.01) | |

(52) U.S. Cl.
CPC .............. *C12M 35/00* (2013.01); *C12Q 1/68* (2013.01); *C12Q 1/6825* (2013.01); *G01N 33/53* (2013.01); *B01L 2300/04* (2013.01); *B01L 2300/0829* (2013.01); *B01L 2300/168* (2013.01)

(58) Field of Classification Search
CPC .......... C12M 35/00; C12Q 1/68; C12Q 1/682; C12Q 1/6825; G01N 33/53
See application file for complete search history.

(56) References Cited

U.S. PATENT DOCUMENTS

| | | | |
|---|---|---|---|
| 7,824,889 B2 | 11/2010 | Vogelstein et al. | |
| 7,915,015 B2 | 3/2011 | Vogelstein et al. | |
| 8,859,206 B2 | 10/2014 | Vogelstein et al. | |
| 2002/0164820 A1* | 11/2002 | Brown ................. | B01L 3/5027 436/180 |
| 2002/0192701 A1* | 12/2002 | Adey .................... | B01F 5/10 435/6.11 |
| 2003/0049862 A1* | 3/2003 | He ........................ | B01L 3/5025 506/16 |
| 2003/0087292 A1* | 5/2003 | Chen .................... | B01F 5/061 435/6.12 |
| 2003/0138941 A1* | 7/2003 | Gong ................... | B01L 3/5027 435/287.2 |
| 2005/0130176 A1 | 6/2005 | Vogelstein et al. | |
| 2006/0134704 A1 | 6/2006 | Muraguchi et al. | |
| 2009/0181859 A1 | 7/2009 | Muraguchi et al. | |
| 2009/0258383 A1 | 10/2009 | Kovac et al. | |
| 2010/0252128 A1 | 10/2010 | Gong et al. | |
| 2012/0238475 A1* | 9/2012 | Leamon ............. | B01L 3/502707 506/16 |
| 2013/0296197 A1* | 11/2013 | Narahara ............. | C12Q 1/6869 506/26 |
| 2015/0038341 A1 | 2/2015 | Vogelstein et al. | |
| 2015/0204785 A1 | 7/2015 | Kim et al. | |

FOREIGN PATENT DOCUMENTS

| | | |
|---|---|---|
| EP | 1 566 635 A1 | 8/2005 |
| EP | 2 891 886 A1 | 7/2015 |
| JP | 4911592 B | 4/2012 |
| WO | WO 2004/051266 A1 | 6/2004 |
| WO | WO 2008/088395 A2 | 7/2008 |
| WO | WO 2009/078812 A1 | 6/2009 |
| WO | WO 2013/176767 A1 | 11/2013 |
| WO | WO 2014/034781 A1 | 3/2014 |

OTHER PUBLICATIONS

Partial European Search Report dated May 24, 2018 in European Patent Application No. 15857010.1, 16 pages.

International Search Report dated Jan. 26, 2016 in PCT/JP2015/081029, filed Nov. 4, 2015.

Zhang, R. et al., "A Microfluidic Liquid Phase Nucleic Acid Purification Chip to Selectively Isolate DNA or RNA from Low Copy/Single Bacterial Cells in Minute Sample Volume Followed by Direct On-chip Quantitative PCR Assay", Analytical Chemistry, 2013, vol. 85, No. 3, p. 1484-1491.

Nomura, S., et al., "Development of a novel nano-Invader DNA chip system", Journal of Biochemical and Biophysical Methods, 2007, vol. 70, issue 5, p. 787-795.

Dube, S. et al., "Mathematical Analysis of Copy Number Variation in a DNA Sample Using Digital PCR on a Nanofluidic Device", PLoS One, 2008, 3(8), e2876, 9 pages.

Kim, S.H. et al., "Large-scale femtoliter droplet array for digital counting of single biomolecules", Lab on a Chip, DOI: 10.1039/c21 c40632b, 2012, 6 pages.

European Office Action dated May 31, 2019 in European Application No. 15857010.1, filed Nov. 4, 2015, 8 pages.

Combined Chinese Office Action and Search Report dated Nov. 28, 2019 in Patent Application No. 201580058902.3 (with English translation of the Office Action and English translation and English translation of categories of cited documents), 19 pages.

* cited by examiner

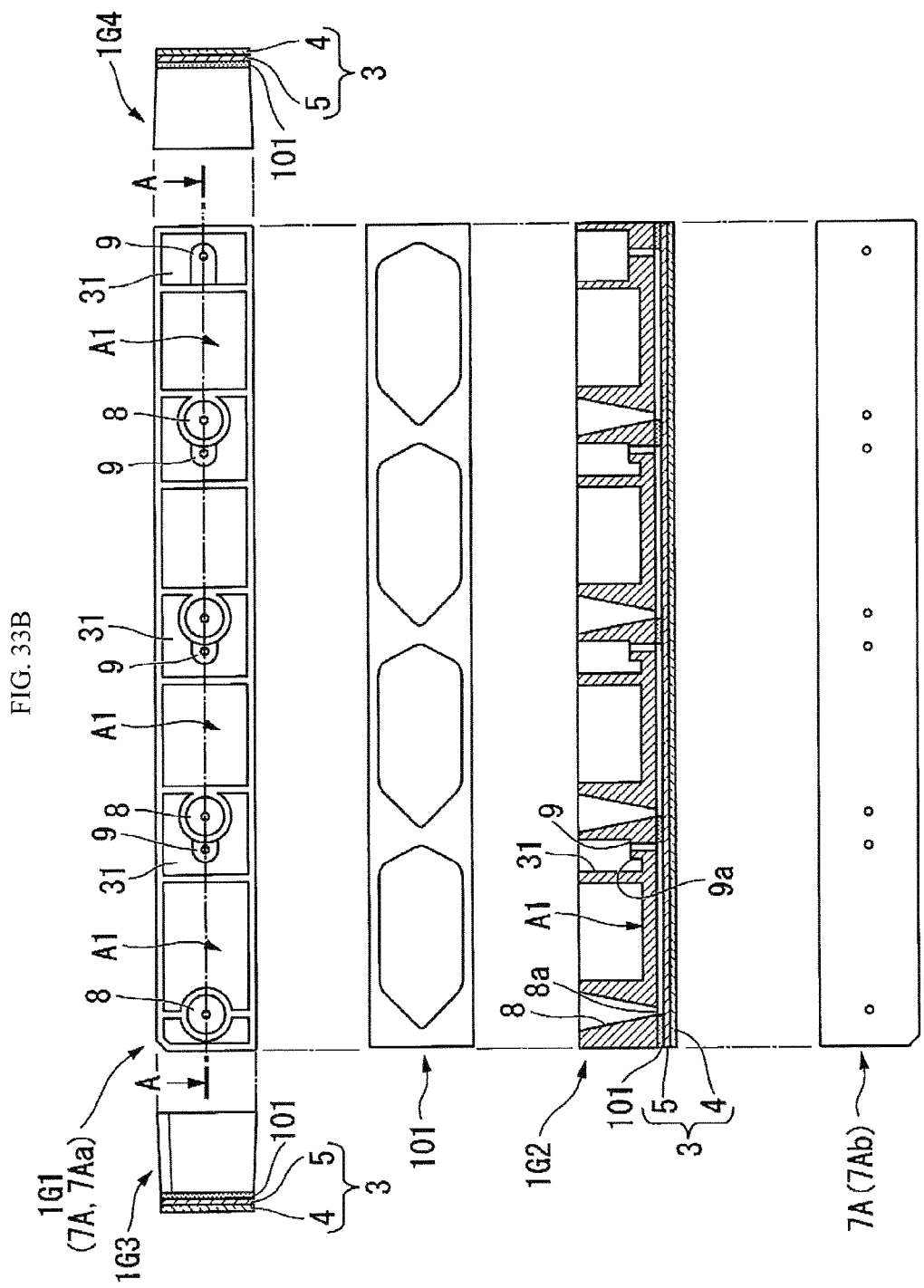

NUCLEIC ACID INTRODUCTION METHOD, NUCLEIC ACID DETECTION METHOD, BIOMOLECULE ANALYSIS METHOD, ARRAY DEVICE FOR BIOMOLECULE QUANTIFICATION, AND BIOMOLECULE ANALYSIS KIT

CROSS-REFERENCE TO RELATED APPLICATIONS

The present application is a continuation of International Application No. PCT/JP2015/081029, filed Nov. 4, 2015, which is based upon and claims the benefits of priority to Japanese Application No. 2014-224639, filed Nov. 4, 2014, and claims the benefits of priority to Japanese Application No. 2015-022624, filed Feb. 6, 2015. The entire contents of these applications are incorporated herein by reference.

BACKGROUND OF THE INVENTION

Field of the Invention

The present invention relates to a nucleic acid introduction method, a nucleic acid detection method, a biomolecule analysis method, an array device for biomolecule quantification, and a biomolecule analysis kit.

Discussion of the Background

It is known that a physical disorder or a physical predisposition can be diagnosed through biomolecule analysis. Examples of such known diagnostic methods include SNP (single nucleotide polymorphism) analysis used for diagnosing physical predispositions, somatic mutation analysis used for determining administration of anticancer drugs, and analysis of proteins or DNA of viruses used for remedying infectious diseases.

For example, therapeutic medications for cancers are supposed to provide an index of therapeutic effects through quantification of the number of copies of an EGFR (epidermal growth factor receptor) variant before and after administration of EGFR-TKI (tyrosine kinase inhibitor). In conventionally used quantifications based on real time PCR, changing the total amount of nucleic acids used for a test has been found to affect the quantitative results. Therefore, digital PCR techniques, for which the total amount of nucleic acids does not affect quantitative results, are now under development.

Such a digital PCR technique is used for quantifying nucleic acids in a sample. Specifically, in the PCR technique, a mixture of a PCR reagent and nucleic acids is divided into many micro droplets. The micro droplets are then subjected to PCR amplification in which nucleic acids to be detected in the nucleic acids of the mixture are used as a template to detect a signal, such as fluorescence, caused by the PCR amplification, from the micro droplets containing the template nucleic acid. Then, the ratio of the micro droplets from which the signal has been detected is calculated, thereby quantifying the nucleic acids in the sample.

For example, Patent Literature 1 or Non-Patent Literature 1 describes causing an enzymatic reaction in a micro chamber having a micro capacity to thereby conduct a test for biomolecules using digital PCR.

Known methods of preparing micro droplets used for digital PCR include a method of segmenting a mixture of a reagent and nucleic acids using a sealing liquid, and a method of injecting a mixture of a reagent and nucleic acids into holes formed in a substrate and then sealing the holes with a sealing liquid. Patent Literature 2 discloses a method of preparing an emulsion in micro chambers to acquire a large volume of experimental data in a short time using a small amount of reagent.

In digital PCR, a mixture of a PCR reagent and nucleic acids is diluted so that the number of template nucleic acids present in one micro droplet is 1 or 0. In digital PCR, the volume of each micro droplet is preferably small to enhance the sensitivity of nucleic acid amplification and to simultaneously amplify nucleic acids using many micro droplets. For example, Non-Patent Literature 1 discloses a microarray reaction vessel having wells each having a capacity of 6 nl. Non-Patent Literature 2 discloses a method using a microarray having channels that are formed with many wells each having a depth of 3 μm and a diameter of 5 μm. In the method, a sample is introduced into the channels to guide the sample into the wells, and then surplus reagent in the channels is expelled with a sealing liquid.

Patent Literature 1: JP 2003-511009 A
Patent Literature 2: JP 4911592 B
Non-Patent Literature 1: PLOS ONE, 3(8), e2876, (2008)
Non-Patent Literature 2: Lab on a Chip, DOI: 10.1039/c21 c40632b, (2012)

SUMMARY OF THE INVENTION

According to an aspect of the present invention, an array device includes a base having wells, a cover positioned over the base with a gap from the base such that openings of the wells are covered by the cover with the gap in between, an injection port communicating with the gap, a discharge port communicating with the gap and positioned apart from the injection port, and a waste liquid vessel which collects liquid that flows from the gap via the discharge port and is positioned at a level different from the gap forming a channel. The discharge port is placed to discharge a surplus aqueous solution outside the wells from the discharge port by an oleaginous sealant to be delivered from the injection port.

According to another aspect of the present invention, a method of introducing a nucleic acid into a well of an array device includes supplying a mixture including a template nucleic acid into a channel of an array device where a plurality of wells are formed in the channel, and an aqueous solution is filled in the channel and the wells, and causing the mixture supplied to the channel to diffuse into the aqueous solution in the wells such that the nucleic acid is introduced into the well of the array device.

According to still another aspect of the present invention, a method of detecting a nucleic acid in a mixture includes supplying a mixture including a template nucleic acid into a channel of an array device where a plurality of wells are formed in the channel, and an aqueous solution is filled in the channel and the wells, causing the mixture supplied to the channel to diffuse into the aqueous solution in the wells such that the nucleic acid is introduced into the well of the array device, supplying an oleaginous sealant into the channel such that the mixture and the aqueous solution are sealed in the wells by the oleaginous sealant, and that the wells form reaction vessels for independently detecting the nucleic acid, and detecting the nucleic acid in the reaction vessels.

According to yet another aspect of the invention, a method of analyzing a biomolecule includes supplying a mixture including a template nucleic acid into a channel of an array device where a plurality of wells are formed in the channel, and an aqueous solution is filled in the channel and the wells, causing the mixture supplied to the channel to diffuse into the aqueous solution in the wells such that the nucleic acid is introduced into the well of the array device, supplying an oleaginous sealant into the channel such that the mixture and the aqueous solution are sealed in the wells by the oleaginous sealant, and that the wells form reaction vessels for independently detecting the nucleic acid, and detecting the nucleic acid in the reaction vessels. The mixture includes at least one of DNA, RNA, miRNA, mRNA, and a protein, as a target substance under analysis, and at least one of the mixture and the aqueous solution includes a labeling substance having a specific labeling function to the target substance in a state where the template nucleic acid is included in the labeling substance or the template nucleic acid is bondable to the labeling substance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 33B is a six-sided view illustrating a configuration of still another modification (Modification 14) of the third embodiment.

DESCRIPTION OF THE EMBODIMENTS

Figure 1:
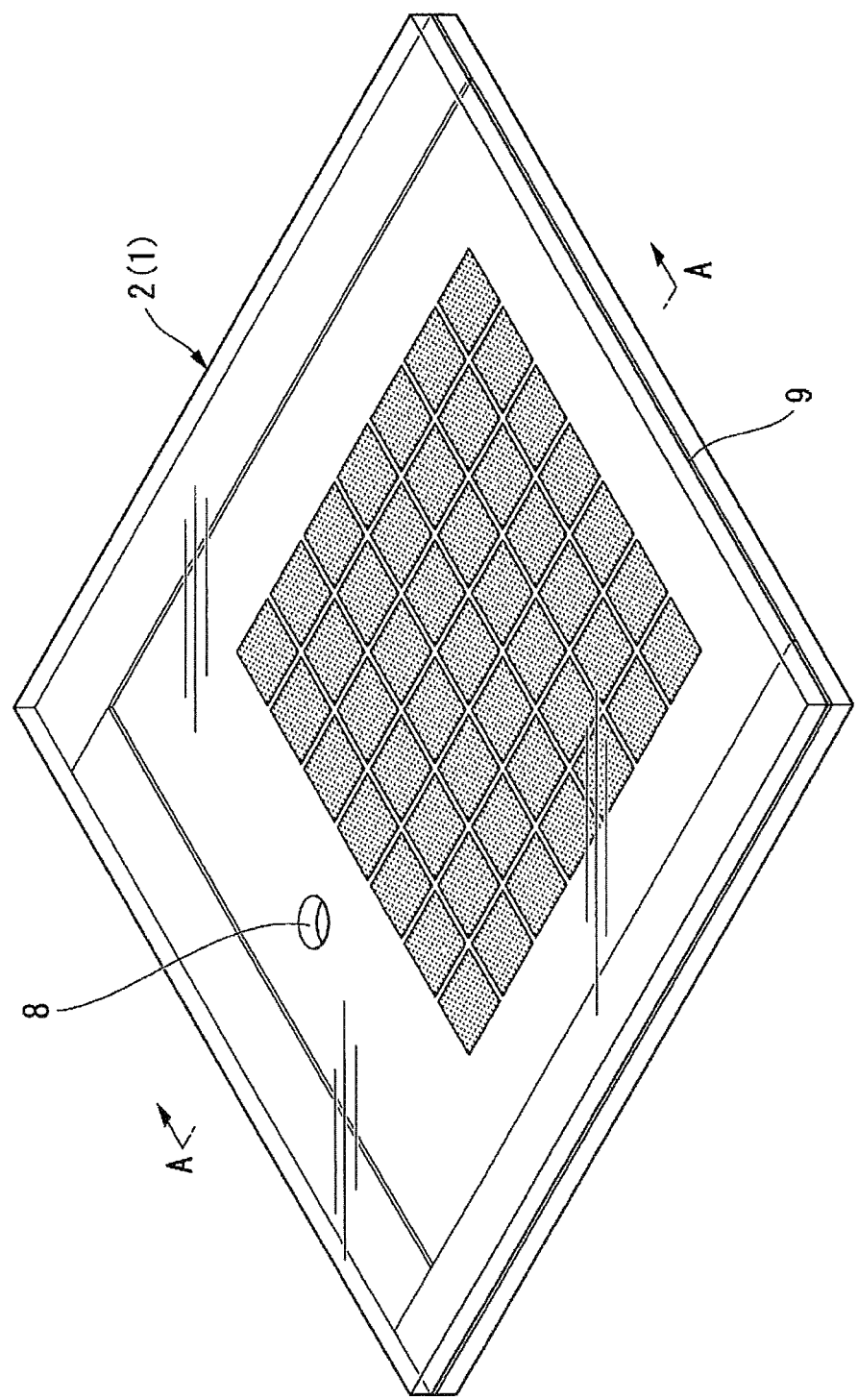
FIG. 1 is a perspective view illustrating a biomolecule analysis kit according to a first embodiment of the present invention.

The embodiments will now be described with reference to the accompanying drawings, wherein like reference numerals designate corresponding or identical elements throughout the various drawings.

First Embodiment

Figure 2:
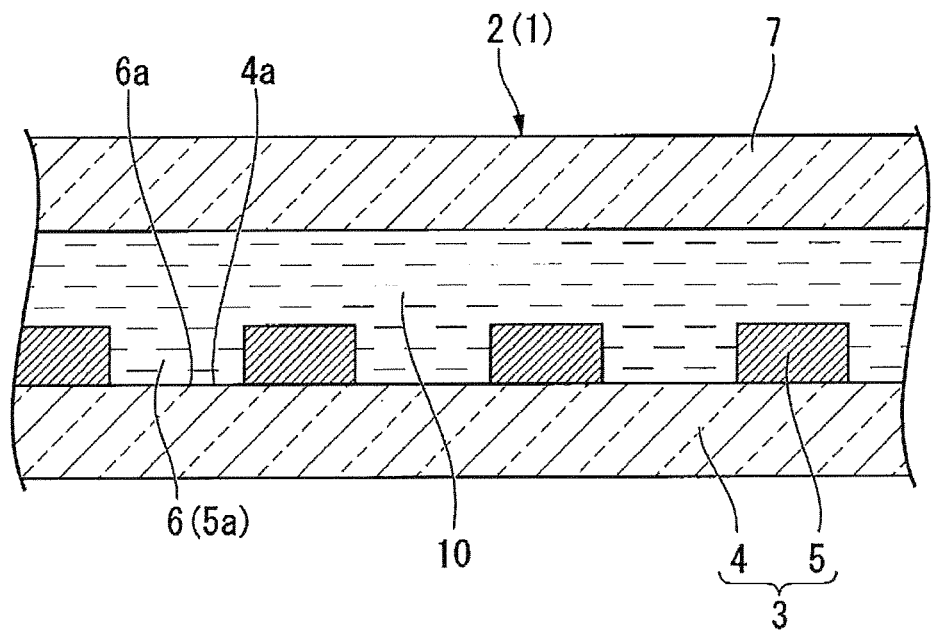
FIG. 2 is a cross-sectional view taken along the line A-A of FIG. 1.
Figure 3:
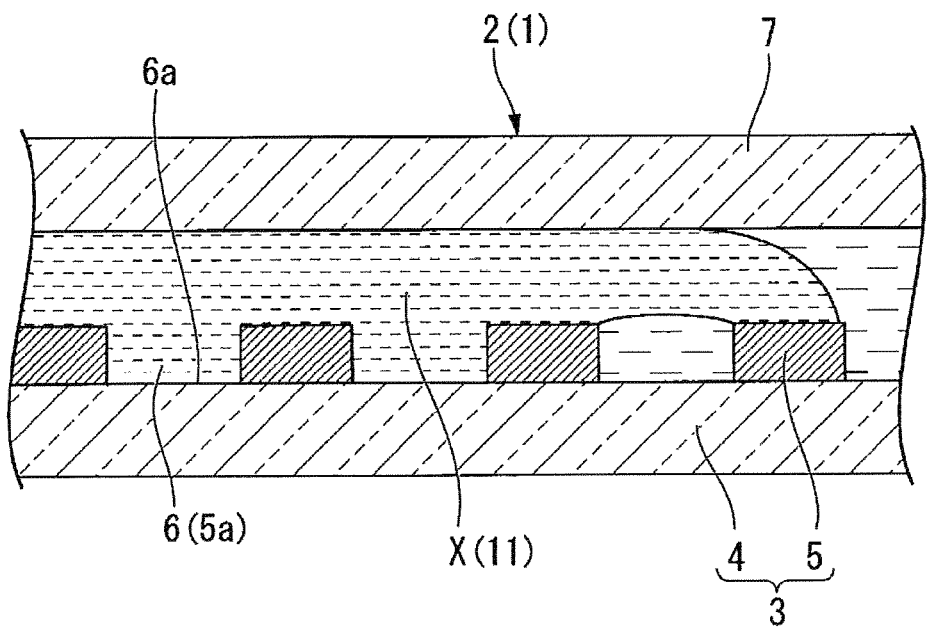
FIG. 3 is a diagram illustrating operation of the biomolecule analysis kit.
Figure 4:
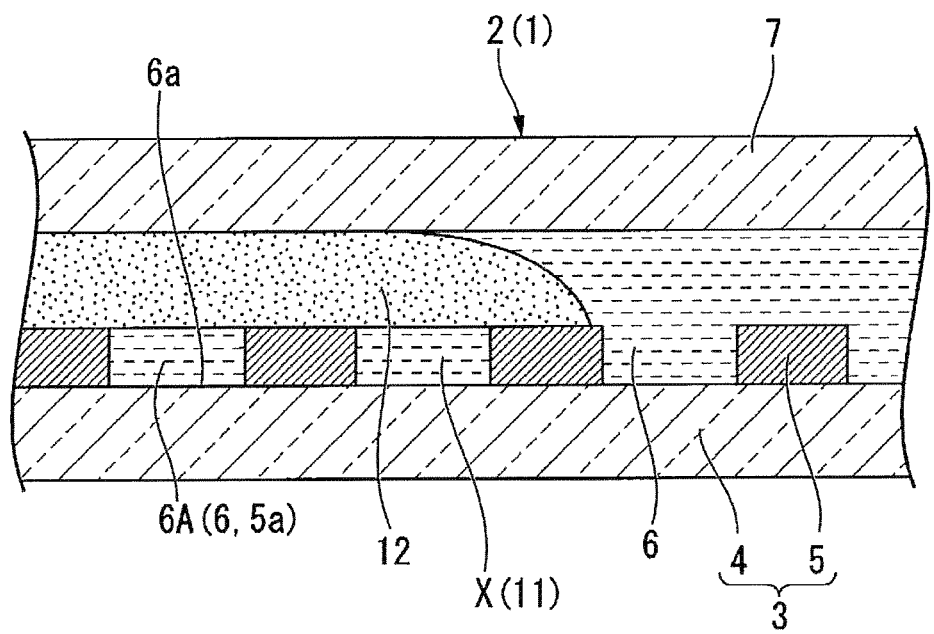
FIG. 4 is a diagram illustrating operation of the biomolecule analysis kit.

Hereinafter will be described a nucleic acid introduction method, a nucleic acid detection method, a biomolecule analysis method, an array device for biomolecule quantification, and a biomolecule analysis kit according to a first embodiment of the present invention. FIG. 1 is a perspective view illustrating a biomolecule analysis kit according to the present embodiment. FIG. 2 is a cross-sectional view taken along the line A-A of FIG. 1. FIGS. 3 and 4 are diagrams illustrating the operation of the biomolecule analysis kit according to the present embodiment.

A biomolecule analysis kit 1 according to the present embodiment includes an array device that quantifies nucleic acids (array device 2 for nucleic acid quantification) as an example of an array device for quantifying biomolecules (array device for biomolecule quantification).

First, a configuration of the biomolecule analysis kit 1 including the array device 2 for nucleic acid quantification according to the present embodiment will be described. The biomolecule analysis kit 1 of the present embodiment shown in FIG. 1 is used for analysis of target substances selected from any of DNA, RNA, miRNA, mRNA, proteins, exosomes, liposomes, and cells. More specifically, the biomolecule analysis kit 1 of the present embodiment quantitatively measures the concentration of an analysis target substance contained in biomolecules.

The biomolecule analysis kit of to the present embodiment includes the array device 2 for nucleic acid quantification shown in FIGS. 1 and 2, a detection reaction reagent 11 (see FIG. 3), and an oleaginous sealing liquid 12 (see FIG. 4) used together with the array device 2.

As shown in FIGS. 1 and 2, the array device 2 includes a base 3 having a plurality of wells 6, a cover 7, an injection port 8, a discharge port 9, and an aqueous solution 10.

As shown in FIG. 2, the base 3 includes a substrate 4 and a microporous array layer 5.

The substrate 4 is a plate member formed of a substantially transparent material. The material of the substrate 4 is a resin or glass, for example. More specifically, the substrate 4 may be formed of polystyrene or polypropylene. The substrate 4 only needs to have sufficient rigidity to avoid being damaged when handled by a device transporting the array device 2 or when manually handled by an operator.

The microporous array layer 5 is formed with a plurality of arrayed through holes 5a. The thickness of the microporous array layer 5 is 3 µm. There is a gap of 100 µm between the microporous array layer 5 and the cover 7. The through holes 5a formed in the microporous array layer 5 are each in a columnar shape with a diameter of 5 µm and a length of 3 µm in the center line direction. (When the through hole 5a has a diameter of 5 µm and a length of 3 µm in the center line direction, the capacity of a micro chamber formed by one through hole 5a is about 100 femtoliters (fl)).

The capacity of each through hole 5a may be appropriately determined. As an example, the capacity of each of the through holes 5a may be 10 picoliters or less. The distance between the center lines of the through holes 5a only needs to be greater than the diameter of each through hole 5a. The through holes 5a are arrayed in the microporous array layer 5 to form a triangular lattice. The method of arranging the through holes 5a is not limited specifically.

Bottomed tubular wells 6, each having a bottom 6a served by the substrate 4, are formed on the base 3. Specifically, the wells 6 are each defined by the through hole 5a formed on the microporous array layer 5, and a surface 4a of the substrate 4.

The material of the microporous array layer 5 may be a resin or glass, for example. The material of the microporous array layer 5 may be the same as or different from the material of the substrate 4. The microporous array layer 5 may be formed of the same material as that of the substrate 4 and integrated therewith. The microporous array layer 5 may be formed of the same material as that of the substrate 4 and integrally formed therewith. Examples of the material of the microporous array layer 5, when formed of a resin, include a cycloolefin polymer, silicon, polypropylene, polycarbonate, polystyrene, polyethylene, polyvinyl acetate, fluorine resin, amorphous fluorine resin, and the like.

These materials of the microporous array layer 5 shown above are only examples and should not be construed in a limiting sense.

For example, the microporous array layer 5 may be formed on a glass substrate 4 using a cycloolefin polymer that is a hydrophobic resin. In this configuration, since the surface of the glass substrate 4 is hydrophilic, a hydrophilic sample is easily held in the wells 6 in heating the sample by Invader reaction for the analysis of the sample.

When the microporous array layer 5 is formed of a hydrophobic material, such as a hydrophobic resin, the hydrophobic site of a biomolecule to be detected is easily adsorbed and held by the hydrophobic microporous array layer 5. Thus, the biomolecules are efficiently trapped by the microporous array layer 5 for easy detection of the biomolecules in the wells 6.

Hydrophobicity in the present embodiment is defined to be that a contact angle of a material with water in a contact angle test is 70° or more.

For example, the contact angle of a material used in the present embodiment with water is 85° when the material is a cycloolefin polymer (COP), or is about 110° when the material is CYTOP, which are hydrophobic resins.

In the contact angle test, a liquid drop method was used.

The microporous array layer 5 may be colored. When the microporous array layer 5 is colored, and when fluorescence, luminescence, absorbance, or the like is measured in the wells 6 using light, the influence of light from other wells 6 near the measurement-target well 6 is reduced.

The microporous array layer 5 is formed with the through holes 5a such as by etching, embossing, or cutting a solid pattern stacked on the substrate 4. When the microporous array layer 5 has been integrally formed with the substrate 4, portions corresponding to the through holes 5a of the microporous array layer 5 are formed such as by etching, embossing, or cutting the substrate 4.

The cover 7 is laid over the base 3 to cover the openings of the plurality of wells 6, with a gap being formed between the base 3 and the cover 7. The gap between the base 3 and the cover 7 serves as a channel through which various liquids are passed. In the present embodiment, various liquids are passed between the base 3 and the cover 7 from the injection port 8 toward the discharge port 9.

The injection port 8 shown in FIG. 1 is in a tubular shape to communicate with the gap between the base 3 and the cover 7. In the present embodiment, the injection port 8 is formed in the cover 7. The injection port 8 may be formed in the base 3.

The discharge port 9, which is provided at a position distanced from the injection port 8, communicates with the gap between the base 3 and the cover 7. In the present embodiment, the discharge port 9 is configured in a portion of the base 3 and the cover 7 so that liquid leaks out of the gap between the base 3 and the cover 7 which is most distanced from the injection port 8 when measured from the injection port 8 along the channel direction of the liquid.

The discharge port 9 may be sealably formed in the base 3 or the cover 7 to have a tubular shape communicating with the gap between the base 3 and the cover 7, at a position distanced from the injection port 8. In this case, the liquid between the base 3 and the cover 7 can be prevented from being evaporated through the discharge port 9. The discharge port 9 may be sealed with a seal or a stopper for blocking the discharge port 9.

As shown in FIG. 2, the aqueous solution 10 is filled in between the base 3 and the cover 7.

The aqueous solution 10 is a liquid having a composition miscible with a sample containing an analysis target substance. In the present embodiment, the aqueous solution 10 is a buffer solution containing no nucleic acid. The aqueous solution 10 only needs to fill the wells 6. In other words, a gas may partially or entirely fill the channel portion between the base 3 and the cover 7.

The detection reaction reagent 11 (see FIGS. 3 and 4) is used for causing a biological reaction with a template nucleic acid related to an analysis target substance. The biological reaction with the template nucleic acid corresponds, for example, to a reaction of causing signal amplification in the presence of a template nucleic acid. The detection reaction reagent 11 of the present embodiment causes an enzymatic reaction with a template nucleic acid. The detection reaction reagent 11 is selected, for example, according to a method that can detect a nucleic acid. For example, a reagent used for an Invader (registered trademark) method, TaqMan (registered trademark) method, or fluorescent probing method, or other methods is included in the biomolecule analysis kit 1, as the detection reaction reagent 11 of the present embodiment.

The oleaginous sealing liquid 12 (see FIG. 4) is a solution deliverable from the injection port 8 (see FIG. 1) to the gap between the base 3 and the cover 7. The oleaginous sealing liquid 12 can be selected from materials that are not miscible with the sample containing the analysis target substance. The oleaginous sealing liquid 12 of the present embodiment is a mineral oil.

The following description addresses the nucleic acid introduction method, the nucleic acid detection method, and the biomolecule analysis method according to the first embodiment of the present invention, through use of the biomolecule analysis kit 1 of the present embodiment, and also addresses the advantageous effects of the biomolecule analysis kit 1 of the present embodiment.

In the present embodiment, as shown in FIG. 2, the injection port 8 (see FIG. 1) and the discharge port 9 (see FIG. 1) of the biomolecule analysis kit 1 are both in a state of being watertightly sealed before use, with the aqueous solution 10 being filled in the gap between the base 3 and the cover 7. Thus, the aqueous solution 10 between the base 3 and the cover 7 is confined between the base 3 and the cover 7 until the injection port 8 or the discharge port 9 is opened.

In the present embodiment, the capacity of each well 6 is very small. Therefore, when the aqueous solution 10 is filled in the wells 6 during manufacture of the array device 2 for nucleic acid quantification, the aqueous solution 10 in the wells 6 (the aqueous solution filled in the wells) is not easily replaced by air if vibration and the like is transmitted to the array device 2 before use of the biomolecule analysis kit 1.

In the present embodiment, when the aqueous solution 10 is filled in the wells 6 beforehand during manufacture of the biomolecule analysis kit 1 (array device 2 for nucleic acid quantification), a process of degassing the biomolecule analysis kit 1 can be eliminated when a user uses the kit 1. Thus, the user can conveniently and easily use the kit 1.

When using the biomolecule analysis kit 1, the sample containing an analysis target substance is appropriately diluted, as pre-treatment, with a known solvent. In diluting the sample, the dilution ratio of a known digital PCR may be referenced. A solvent used for diluting the sample containing an analysis target substance preferably has a composition miscible with the aqueous solution 10 filled in the wells 6 (the aqueous solution filled in the wells). In the process of diluting the sample containing an analysis target substance, the detection reaction reagent 11 is mixed at a prescribed concentration.

The following description addresses an example of conducting a signal amplification reaction by means of an Invader method using a nucleic acid, which is an analysis target substance, as a template nucleic acid. The template nucleic acid may be a nucleic acid produced by a biological body, or may be an artificial material, such as a product of PCR (polymerase chain reaction). The template nucleic acid may be an antibody that can trap biomolecules, or may be a labeled nucleic acid in antibody labeled beads. In the case in which part of or the entire detection reaction reagent 11 is contained in the aqueous solution 10, part of or the entire process of mixing the detection reaction reagent 11 in the pre-treatment is not necessary.

First, the injection port 8 and the discharge port 9 shown in FIG. 1 are opened. Then, a mixed solution X of the sample containing a template nucleic acid and the detection reaction reagent 11 for the Invader reaction is delivered to the gap between the base 3 and the cover 7 through the injection port 8 using a dispensing pipette, or the like. The mixed solution X of the sample and the detection reaction reagent 11 spreads out in the gap between the base 3 and the cover 7 to cover all the plurality of wells 6 (see FIG. 3). Delivery of the mixed solution X of the sample and the detection reaction reagent 11 to the gap between the base 3 and the cover 7 causes discharge of the aqueous solution 10 from the discharge port 9. In this case, the mixed solution X of the sample and the detection reaction reagent 11 may be colored differently from the color of the aqueous solution 10, so that the different coloring can indicate the delivered areas of the mixed solution X of the sample and the detection reaction reagent 11 in the gap between the base 3 and the cover 7.

As shown in FIG. 3, the plurality of wells 6 formed of the substrate 4 and the microporous array layer 5 are arranged in the channel configured by the base 3 and the cover 7. The aqueous solution 10 filled in the plurality of wells 6 (the aqueous solution filled in the wells) is retained being held by the inner surfaces of the wells 6. Thus, the mixed solution X of the sample and the detection reaction reagent 11 is laid over the aqueous solution 10 without replacing the aqueous solution 10 filled in the plurality of wells 6. The aqueous solution 10 however is easily miscible with the mixed solution X and therefore, after the mixed solution X has been laid over the aqueous solution 10, the solute in the mixed solution X diffuses into the aqueous solution 10 (the aqueous solution filled in the wells).

Subsequently, as shown in FIG. 4, the oleaginous sealing liquid 12 is delivered from the injection port 8 (see FIG. 1) into the channel configured by the base 3 and the cover 7. The oleaginous sealing liquid 12 seals the liquid in the plurality of wells 6 (the aqueous solution filled in the wells), with the mixed solution X being diffused in the aqueous solution 10, to turn the plurality of wells 6 into a plurality of independent nucleic acid detection reaction vessels 6A. Also, the liquid on the outside of the plurality of wells 6 in the gap between the base 3 and the cover 7 is expelled from the discharge port 9 by the oleaginous sealing liquid 12.

Due to the dilution of the sample as pre-treatment, the number of molecules of the template nucleic acid is 1 or 0 in each nucleic acid detection reaction vessel 6A. If the concentration of the sample is too high, several molecules of the template nucleic acid may be trapped by each nucleic acid detection reaction vessel 6A.

In the present embodiment, the detection reaction reagent 11 for the Invader reaction and the template nucleic acid are sealed in the wells 6 (in the nucleic acid detection reaction vessels 6A), according to the concentration of the template nucleic acid. In this state, the array device 2 for nucleic acid quantification is incubated in an oven at 62° C. for a predetermined time period. Incubation of the array device 2 in the oven at 62° C. for a predetermined time period favorably progresses the signal amplification in the Invader reaction which is isothermally conducted (isothermal reaction) in the nucleic acid detection reaction vessels 6A.

Subsequently, the array device 2 in which the detection reaction reagent 11 for the Invader reaction and the template nucleic acid are sealed in the wells 6 (nucleic acid detection reaction vessels 6A) is unloaded from the oven after the predetermined time period, for measurement of the number of the nucleic acid detection reaction vessels 6A having fluorescence and the amount of fluorescence of the nucleic acid molecules having fluorescence. In the present embodiment, an amount of fluorescence exceeding a predetermined S/N ratio in relation to autofluorescence may be used as a threshold for the presence/absence of fluorescence in the nucleic acid detection reaction vessels 6A. In the present embodiment, if the signal amplification by the Invader method favorably progresses to thereby saturate signals in the nucleic acid detection reaction vessels 6A, large variation is unlikely to occur in the amount of fluorescence among the nucleic acid detection reaction vessels 6A having fluorescence.

As described above, the liquid containing a template nucleic acid is introduced from the injection port 8 to the gap between the base 3 and the cover 7 in the nucleic acid introduction method, the nucleic acid detection method, the biomolecule analysis method, the array device 2 for nucleic acid quantification, and the biomolecule analysis kit 1 according to the present embodiment. Thus, the surplus aqueous solution 10 outside the plurality of wells 6 is discharged from the discharge port 9, while the template nucleic acid is transferred by diffusion to the aqueous solution 10 in the plurality of wells 6 (the aqueous solution 10 filled in the wells). Consequently, according to the nucleic acid introduction method, the nucleic acid detection method, the biomolecule analysis method, the array device 2 for nucleic acid quantification, and the biomolecule analysis kit 1 of the present embodiment, air bubbles are unlikely to enter the wells 6 in the transfer of the template nucleic acid to the wells 6.

In the present embodiment, the probability of the air bubbles entering the wells 6 is quite low. The nucleic acid detection method, the biomolecule analysis method, the array device 2 for nucleic acid quantification, and the biomolecule analysis kit 1 of the present embodiment can minimize variation in the number of the nucleic acid detection reaction vessels 6A that can detect nucleic acid molecules, due to the presence of air bubbles. If the capacity of each well 6 is quite small, the volume of air bubbles in the well 6 is significant, leading to possible variation in the progress of nucleic acid detection reactions between the wells 6. However, in the present embodiment, it is not necessary to consider the presence of air bubbles in the wells 6, eliminating the necessity of removing air bubbles from the wells 6 and enabling highly accurate quantitative analysis with simple and easy manipulation.

Besides the detection of fluorescence, a system for detecting visible light luminescence or color development, or the like as a signal may be applied to the present embodiment.

The configuration of the present embodiment may also be applied to the analysis of a protein. When analyzing a protein, the molecule specifically bonded to a target protein is modified with a nucleic acid, such as a DNA chain. In this case, oligo design may be applied to the Invader method to use a nucleic acid, such as a DNA chain, used for modification as a template nucleic acid, whereby the presence/absence of the target protein can be analyzed using the signal detection procedure of the present embodiment. For example, the substance for analysis may be any of DNA, RNA, miRNAs, mRNA, or proteins. In this case, the substance quantified by the array device 2 for nucleic acid quantification, and the biomolecule analysis kit 1 of the present embodiment corresponds to a nucleic acid, such as a DNA chain, used for modification. The substance modified by the nucleic acid is indirectly quantified. The substance to be modified with a molecule specifically bonded to a target protein is not limited to a DNA chain, but may be at least a substance that generates a signal for detection. For example, fluorescent beads, HRP (horseradish peroxidase), and the like can be mentioned.

A substance to which the substance modified with a template nucleic acid as a labeling substance is specifically bonded (substance to be bonded to) may be analyzed by the nucleic acid detection method, the biomolecule analysis method, the array device 2 for nucleic acid quantification, and the biomolecule analysis kit 1 of the present embodiment. In this case, the substance modified with the template nucleic acid may contain at least one of a DNA chain, enzyme, particle, antibody, and liposome different from the template nucleic acid.

Instead of the template nucleic acid, a liquid containing tissue-derived biomolecules which response to fluorescence, visible light, or color development in the wells 6 can be introduced from the injection port 8 to the gap between the base 3 and the cover 7 to quantify the tissue-derived biomolecules.

Examples of the tissue-derived biomolecules quantified as an analysis target substance include liposomes, exosomes, and cells. A substance specifically present in the tissue-derived biomolecules may be fluorescent-labeled, or labeled with something else to enable quantification of the tissue-derived biomolecules. Examples of the substance labeled in this way include a substance that contains a component, such as a low-molecular-weight ligand or an antibody, which is specifically bonded to tissue-derived biomolecules serving as an analysis target substance.

Instead of quantifying an analysis target substance via a template nucleic acid, a signal emitted from tissue-derived biomolecules serving as an analysis target may be detected using the array device for biomolecule quantification of the present embodiment to quantify the tissue-derived biomolecules.

Examples of such tissue-derived biomolecules include cells having a chromosome or other gene regions integrated with a genetically modified fluorescent protein expression cassette that contains a promoter, a target gene, and the like for expressing a fluorescent protein, and cells holding a plasmid or the like that contains the fluorescent protein expression cassette.

For example, a predetermined reagent that promotes transfer to the fluorescent protein expression cassette may be mixed with the cell as mentioned above in each well 6 to permit a fluorescent protein to be expressed, thereby enabling quantification of the cell emitting fluorescence. The fluorescent protein expression cassette may be formulated as an expression cassette for a reporter gene which expresses conforming to the expression of a gene other than a fluorescent protein. In this case, intracellular signal transduction may occur in the wells 6 to express a predetermined gene in conformity with the presence of an extracellular ligand and other signal transfer. The cell in such a well 6 producing the intracellular signal transduction may be quantified using the fluorescence emitted from the fluorescent protein derived from the reporter gene and using the array device for biomolecule quantification of the present embodiment.

As described above, the wells 6 sealed with the oleaginous sealing liquid 12 become independent signal detection vessels for detecting signals from the tissue-derived biomolecules to enable quantification of the tissue-derived biomolecules.

Using the quantification method as described above, viruses or cells present in a biological body can also be quantified as tissue-derived biomolecules. Also, the presence/absence of viruses or cells can be quantitatively confirmed.

The array device for biomolecule quantification of the present embodiment can also quantify substances which are not biomolecules. For example, the array device for biomolecule quantification of the present embodiment can be used as a viral particle quantification device.

Instead of the Invader method disclosed in the present embodiment, another method of signal amplification based on an enzymatic reaction may be adopted, using a signal amplification reaction reagent different from the Invader method. Similarly to the embodiment described above, the signal amplification reaction reagent may be mixed with a sample containing an analysis target substance.

In the example disclosed in the present embodiment, the bottom parts 6a of the plurality of wells 6 and the cover 7 are both made of a substantially transparent material. However, as long as at least either the bottom parts 6a of the plurality of wells 6 or the cover 7 have optical transparency, fluorescence, luminescence, absorbance, and the like can be optically detected in the plurality of wells 6.

The present embodiment discloses a configuration which is preferable when a sample containing a template nucleic acid is aqueous (polar). However, when a sample containing a template nucleic acid is oleaginous (nonpolar), a nonpolar sealing liquid containing an organic solvent, for example, is preferably adopted, instead of the aqueous solution 10. Moreover, when a sample containing a template nucleic acid is oleaginous (nonpolar), a polar replacement solution is preferably used, instead of the oleaginous sealing liquid 12 of the present embodiment, to seal the wells 6. For such solutions, types of solvents may be selected according to solubility of a sample that contains a template nucleic acid in the solvent, and stability of the template nucleic acid and the analysis target. For example, when a sample containing a template nucleic acid is an aqueous solution, a mineral oil can be selected as a sealing liquid. When a sample containing a template nucleic acid uses a mineral oil as a solvent, the water, aqueous buffer solution, or the like, can be selected as a sealing liquid.

Being polar molecules, nucleic acids are insoluble to nonpolar solvents. For example, when a protein or lipid is an analysis target substance, the solubility of the labeled nucleic acid to a solvent as well as the solubility of the analysis target substance to the solvent is preferably considered if the labeled nucleic acid for quantifying the analysis target substance is in a state of being coupled to the analysis target substance. In this case, a sample containing a template nucleic acid (labeled nucleic acid) may be diluted with a nonpolar solvent.

Second Embodiment

Figure 5:
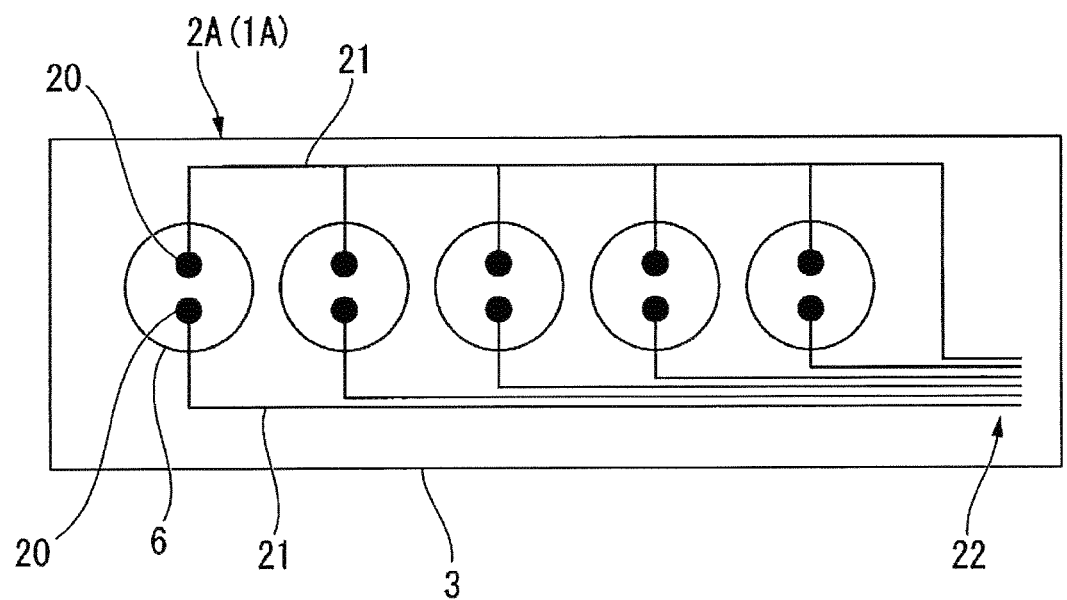
FIG. 5 is a schematic diagram illustrating a base of an array device for nucleic acid quantification in a biomolecule analysis kit according to a second embodiment of the present invention.

Hereinafter, a second embodiment of the present invention will be described. FIG. 5 is a schematic diagram of a base of an array device for nucleic acid quantification in a biomolecule analysis kit according to the present embodiment. It should be noted that like reference signs of the first embodiment are used to describe like components of the present and the subsequent embodiments to omit duplicate description.

A biomolecule analysis kit 1A of the present embodiment shown in FIG. 5 has a configuration different from that of the first embodiment in that an array device 2A for nucleic acid quantification that can conduct electrochemical measurement in the wells 6 is provided replacing the array device 2 for nucleic acid quantification of the first embodiment.

The array device 2A of the present embodiment includes the base 3, the wells 6, the cover 7, the aqueous solution 10, the injection port 8, and the discharge port 9, as disclosed in the first embodiment.

The plurality of wells 6 of the present embodiment have electrodes 20 on the respective bottom parts 6a. The base 3 of the present embodiment includes wires 21 connected to the electrodes 20 of the respective wells 6 and a connector 22 for connecting the wires 21 to a detection circuit.

The electrodes 20 detect a potential change and electrical resistance fluctuation of the solution in the wells 6, for example.

The wires 21 and the connector 22 are formed on the base 3 by printing, for example. As an example, the wires 21 and the connector 22 are patterned on an outer surface of the substrate 4 so that the wires 21 and the connector 22 are sandwiched between the substrate 4 and the microporous array layer 5.

The materials of the electrodes 20, the wires 21, and the connector 22 are not limited specifically.

In the present embodiment, nucleic acids can be quantified based on signals of pH change or potential change corresponding to the presence/absence of a template nucleic acid using the electrodes on the bottom part 6a of each well 6.

Third Embodiment

Figure 6:
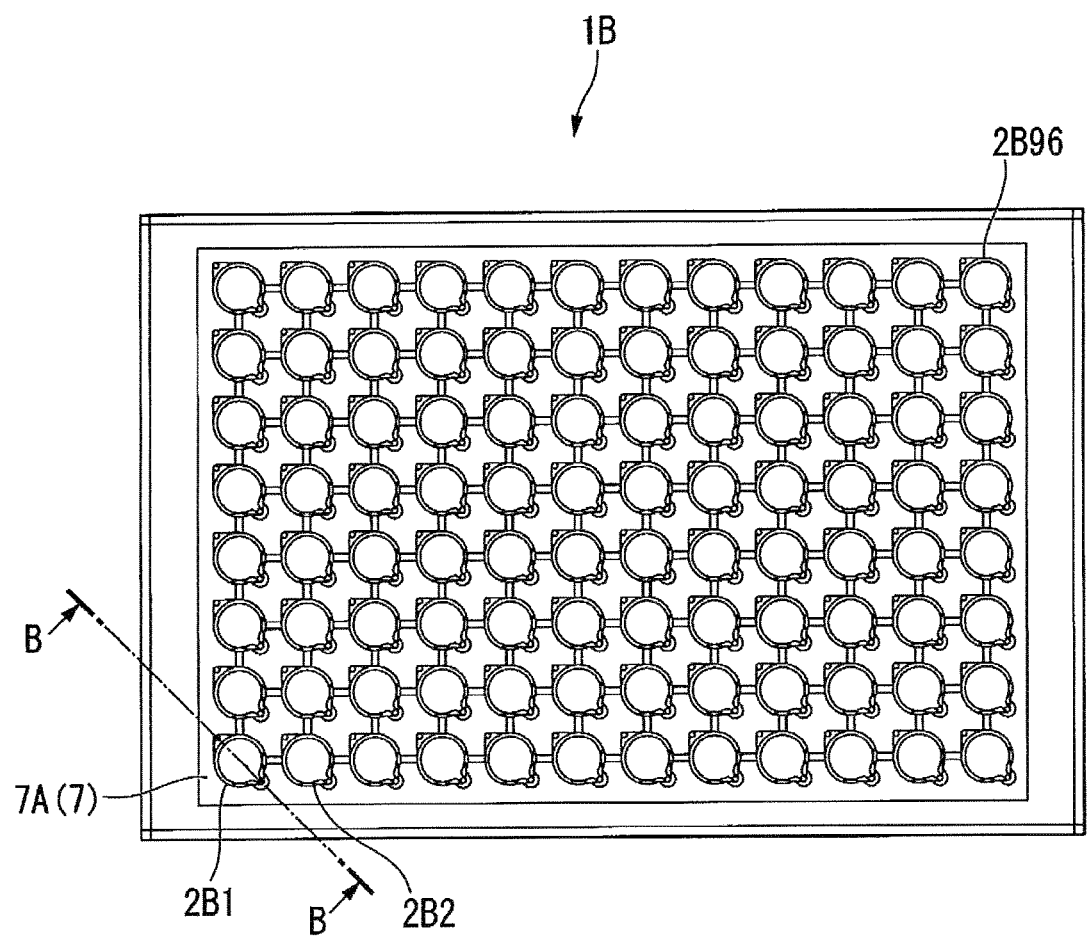
FIG. 6 is a plan view illustrating an array device for nucleic acid quantification in a biomolecule analysis kit according to a third embodiment of the present invention.
Figure 7:
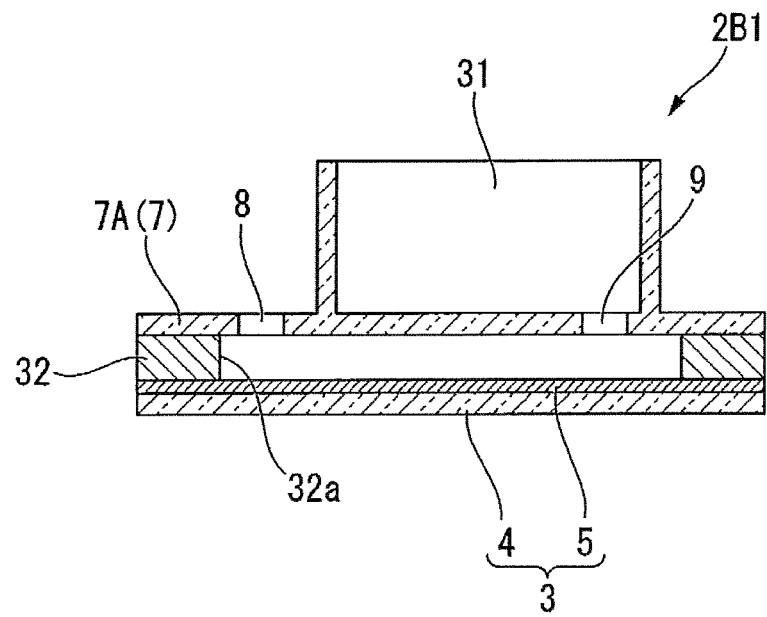
FIG. 7 is a cross-sectional view taken along the line B-B of FIG. 6.

A third embodiment of the present invention will be described. FIG. 6 is a plan view of an array device for nucleic acid quantification in a biomolecule analysis kit of the present embodiment. FIG. 7 is a cross-sectional view taken along the line B-B of FIG. 6.

A biomolecule analysis kit 16 of the present embodiment shown in FIG. 6 includes the base 3, the microporous array layer 5 having wells, the cover 7, the aqueous solution 10, the injection port 8, and the discharge port 9, as disclosed in the first embodiment. The biomolecule analysis kit 1B of the present embodiment further includes a waste liquid vessel 31 communicating with the discharge port 9.

The waste liquid vessel 31, which is disposed outside the cover 7, has a space where liquid is collected from the gap between the base 3 and the cover 7 via the discharge port 9. Replacing the cover 7 of the first embodiment, the present embodiment includes a cover 7A in which the injection port 8, the discharge port 9, and the waste liquid vessel 31 are formed.

Replacing the array device 2 for nucleic acid quantification of the first embodiment, the present embodiment is provided with a plurality of independent array devices 2B1, 2B2, . . . , B96 for nucleic acid quantification (96 devices in the present embodiment). The array devices 2B1, 2B2, . . . , B96 are arranged in a square grid and connected to one another. The plurality of independent array devices 2B1, B2, . . . , B96 are watertightly sectioned by a spacer member 32 connecting the base 3 to the cover 7A. The spacer member 32 of the present embodiment holds the microporous array layer 5 of the base 3 and the cover 7A to provide a 100 µm gap between the microporous array layer 5 and the cover 7A. The spacer member 32 of the present embodiment includes through holes 32a each connecting the injection port 8 to the discharge port 9 and surrounding through holes 5a of the microporous array layer 5.

In the present embodiment, since various liquids discharged from the discharge port 9 are collected in the waste liquid vessel 31, waste liquids can be easily treated.

The biomolecule analysis kit 1B of the present embodiment does not have to necessarily include the aqueous solution 10.

It should be noted that various liquids may be injected from the discharge port 9, and surplus liquids may be discharged from the injection port 8 instead.

(Modification 1)

Figure 8:
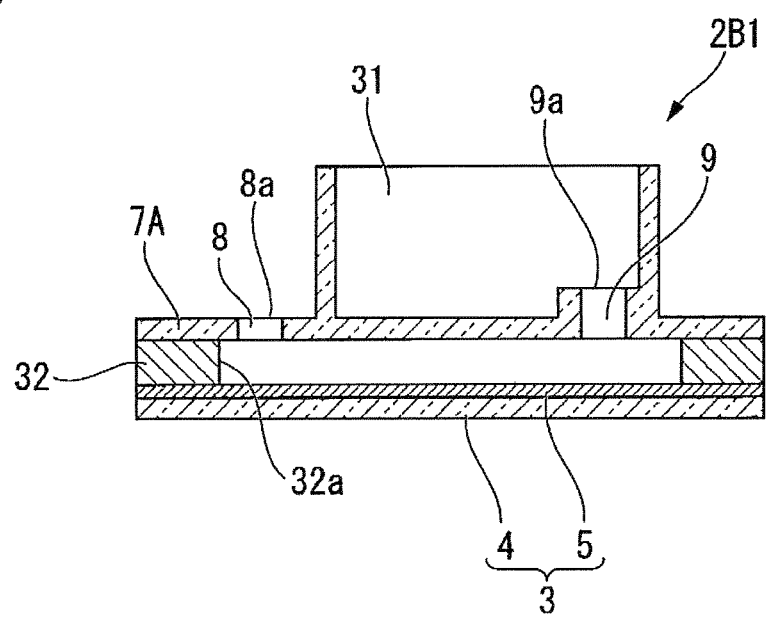
FIG. 8 is a cross-sectional view illustrating a configuration of a modification (Modification 1) of the third embodiment.

Modification 1 of the present embodiment will be described. FIG. 8 is a cross-sectional view illustrating a configuration of the present modification.

In the present modification, the base 3 is defined to be on a lower side and the cover 7A is defined to be on an upper side in the thickness direction of the base 3. As shown in FIG. 8, the level of an injection port opening end 8a of the injection port 8 is lower than the level of a waste liquid vessel side opening end 9a of the discharge port 9. Moreover, the waste liquid vessel side opening end 9a of the discharge port 9 is at a level higher than the level of the bottom surface of the waste liquid vessel 31.

In the present modification, various liquids are permitted to flow in from the injection port opening end 8a before the liquids enter the waste liquid vessel 31 from the waste liquid vessel side opening end 9a of the discharge port 9. Then, when the injection port opening end 8a is opened, gravity causes the liquid level of the injection port 8 to equalize with that of the discharge port 9, during which the liquids flow back from the injection port opening end 8a, with the liquid amount in the discharge port 9 being the upper limit. Thus, air bubbles, if present near the injection port opening end 8a, are swept away by the backflow liquids, and expelled from the injection port opening end 8a. In the present modification, air bubbles are unlikely to remain in the gap between the base 3 and the cover 7A, in the vicinity of the injection port 8.

In the present modification, the waste liquid vessel side opening end 9a of the discharge port 9 is at a level higher than the bottom surface of the waste liquid vessel 31. Thus, the liquids that have entered the waste liquid vessel 31 are unlikely to flow back into the gap between the base 3 and the cover 7A via the discharge port 9.

(Modification 2)

Figure 9:
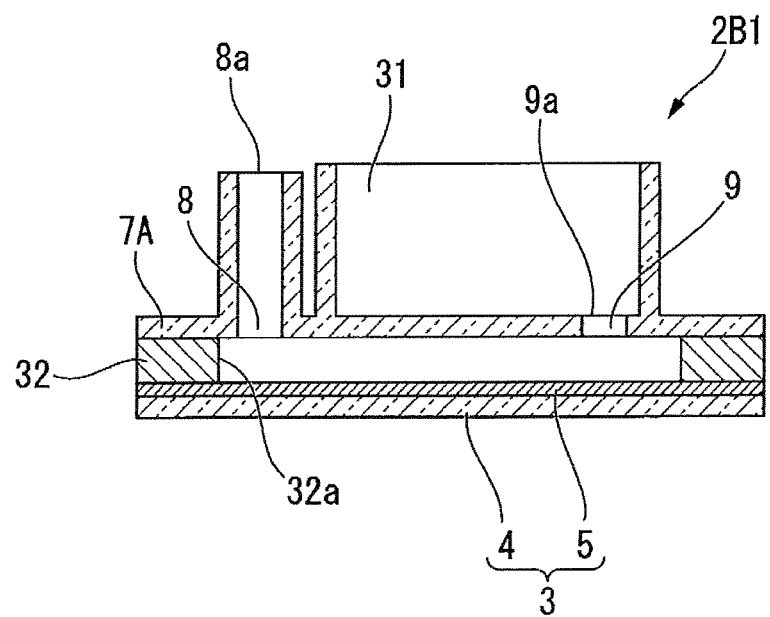
FIG. 9 is a cross-sectional view illustrating a configuration of another modification (Modification 2) of the third embodiment.

Modification 2 of the present embodiment will be described. FIG. 9 is a cross-sectional view illustrating a configuration of the present modification.

In the present modification, the base 3 is defined to be on a lower side and the cover 7A is defined to be on an upper side in the thickness direction of the base 3. As shown in FIG. 9, the level of an injection port opening end 8a of the injection port 8 is higher than the level of a waste liquid vessel side opening end 9a of the discharge port 9. In the present modification, various liquids are permitted to flow in from the injection port opening end 8a before the liquids enter the waste liquid vessel 31 from the waste liquid vessel side opening end 9a of the discharge port 9. Then, when the injection port opening end 8a is opened, gravity causes the liquid level of the injection port 8 to equalize with that of the discharge port 9, during which the liquids in the injection port 8 further enter the gap between the base 3 and the cover 7A. When the mixed solution X of the sample and the detection reaction reagent 11 as well as the oleaginous sealing liquid 12 is delivered to the gap between the base 3 and the cover 7A via the injection port 8, the liquids expelled from the discharge port 9 into the waste liquid vessel 31 could possibly partially return from the discharge port 9 to the gap between the base 3 and the cover 7A due to gravity. However, the liquids are counterbalanced with the mass of the liquids in the injection port 8, to prevent the backflow of the liquids from the waste liquid vessel 31.

(Modification 3)

Figure 10:
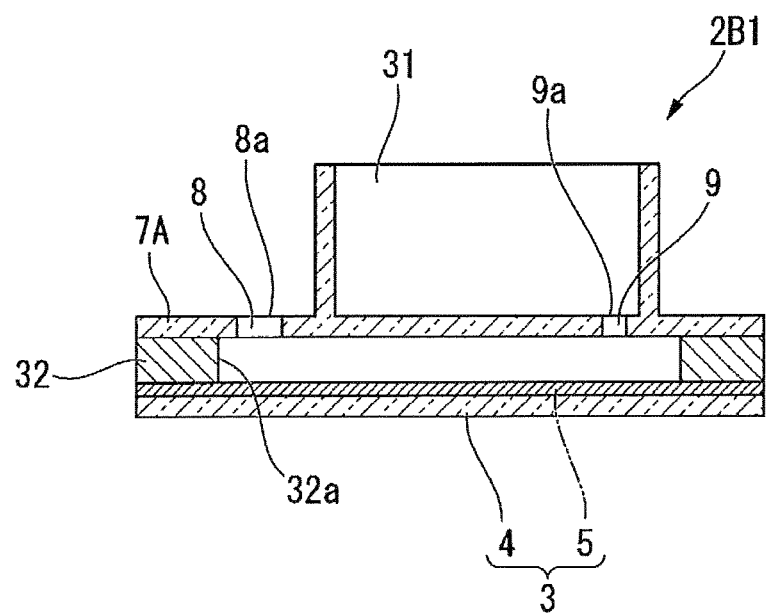
FIG. 10 is a cross-sectional view illustrating a configuration of still another modification (Modification 3) of the third embodiment.

Modification 3 according to the present embodiment will be described. FIG. 10 is a cross-sectional view illustrating a configuration of the present modification.

As shown in FIG. 10, the opening area of the discharge port 9 of the present modification is smaller than that of the injection port 8.

The opening area of the discharge port 9 is determined so as to obtain a channel resistance not allowing passage of liquids through the discharge port 9 unless a liquid delivery pressure is applied from the injection port 8. The specific opening area of the discharge port 9 may be determined according to the composition of the liquids assumed to be discharged from the discharge port 9.

In the present modification, liquids are movable from the gap between the base 3 and the cover 7A during delivery of the liquids from the injection port 8 to the waste liquid vessel 31 via the discharge port 9. After the end of delivery of the liquids from the injection port 8 to the gap, liquids do not flow though the discharge port 9. Thus, the present modification can prevent the backflow of liquids from the waste liquid vessel 31 to the gap between the base 3 and the cover 7A.

It should be noted that various liquids may be injected from the discharge port 9, and surplus liquids may be discharged from the injection port 8 instead.

(Modification 4)

Figure 11:
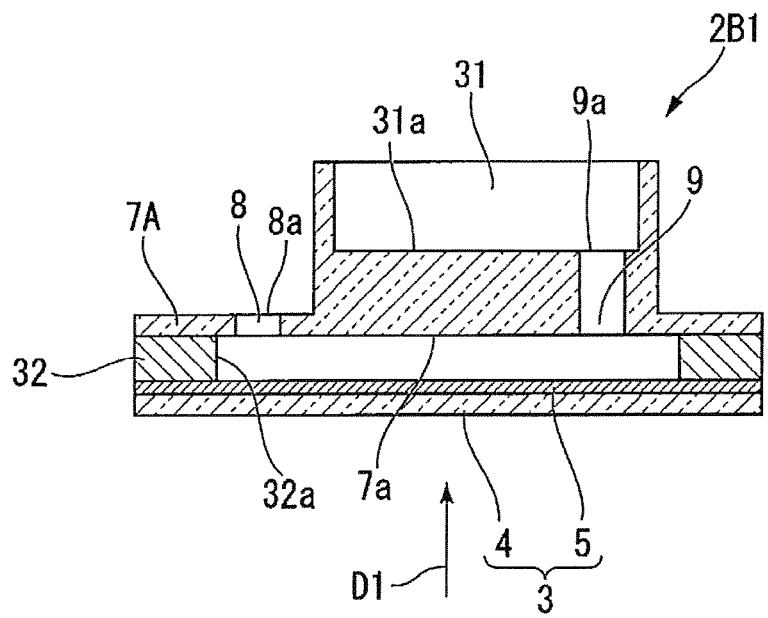
FIG. 11 is a cross-sectional view illustrating a configuration of still another modification (Modification 4) of the third embodiment.

Modification 4 of the present embodiment will be described. FIG. 11 is a cross-sectional view illustrating a configuration of the present modification.

As shown in FIG. 11, in the present modification, the portion configuring a bottom surface 31a of the waste liquid vessel 31 has a large thickness, compared to the biomolecule analysis kit 1B of the third embodiment. Similarly to Modification 1, in the present modification, when the base 3 is defined to be on a lower side and the cover 7A is defined to be on an upper side of the base 3 in the thickness direction, the level of the injection port opening end 8a of the injection port 8 is lower than the level of the waste liquid vessel side opening end 9a of the discharge port 9. With the level of the injection port opening end 8a of the injection port 8 being made lower than the level of the waste liquid vessel side opening end 9a of the discharge port 9, the present modification achieves advantageous effects similarly to those of Modification 1. The level of the injection port opening end 8a of the injection port 8 may be made higher than the level of the waste liquid vessel side opening end 9a of the discharge port 9. In this case, the present modification achieves advantageous effects similarly to those of Modification 2.

In the present modification, when fluorescence, luminescence, or color development, for example, is to be detected from the lower side (the lower face) of the base 3 in the thickness direction (direction indicated by the reference sign D1 in FIG. 11), the portion configuring the large-thickness bottom surface 31*a* of the waste liquid vessel 31 can mitigate the influence of the fluorescence from the waste liquid collected to the waste liquid vessel 31, or the influence of the color of the waste liquid, or the like.

It should be noted that various liquids may be injected from the discharge port 9, and surplus liquids may be discharged from the injection port 8 instead.

(Modification 5)

Figure 12:
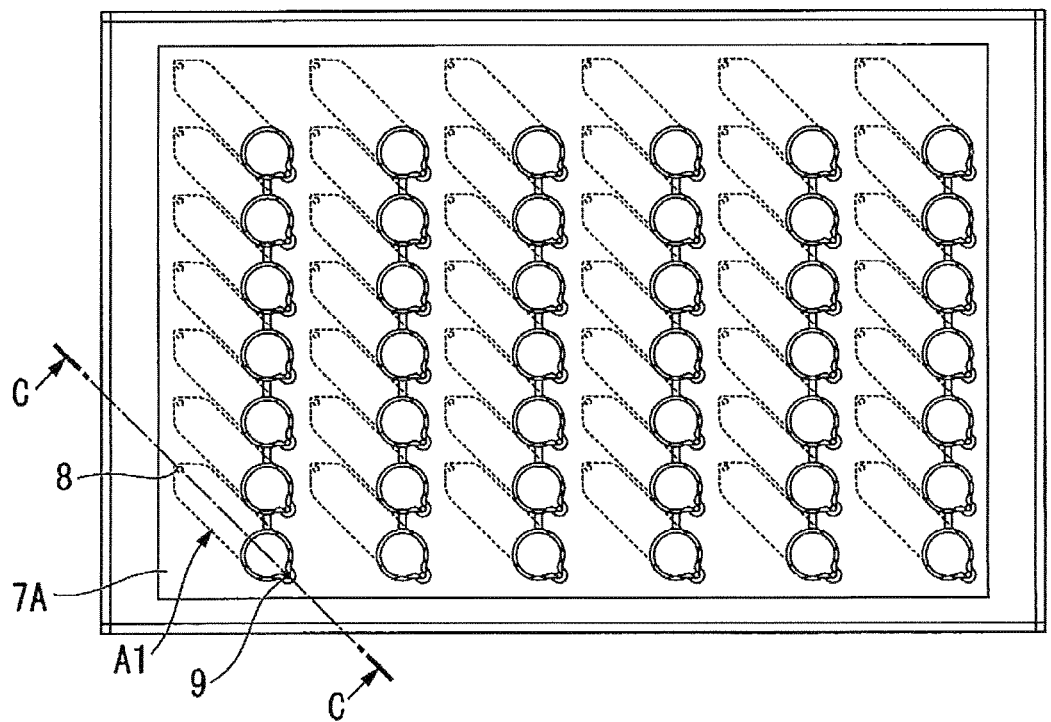
FIG. 12 is a plan view illustrating a configuration of still another modification (Modification 5) of the third embodiment.
Figure 13:
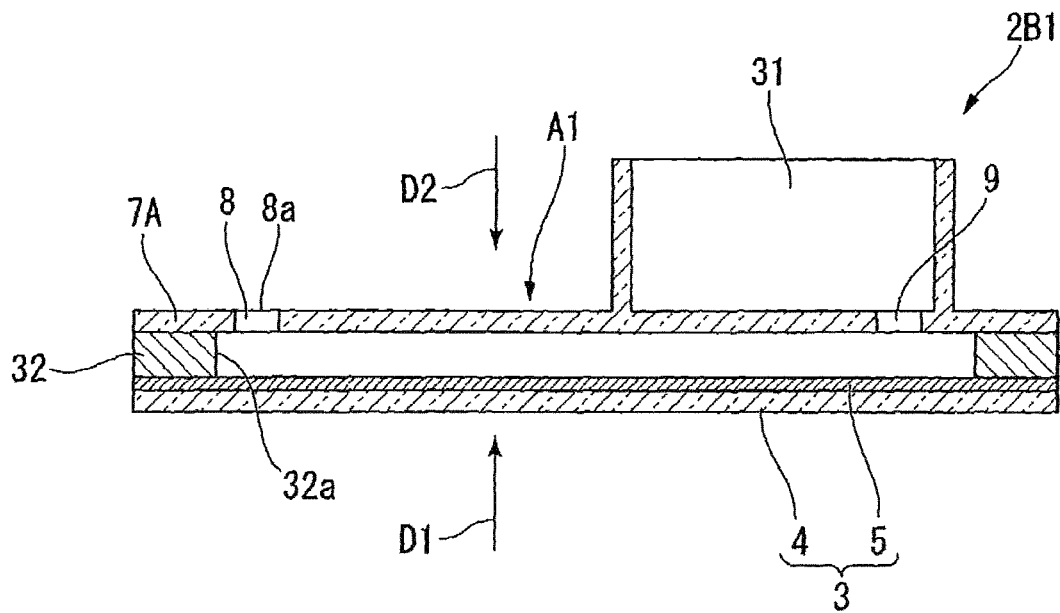
FIG. 13 is a cross-sectional view taken along the line C-C of FIG. 12.

Modification 5 of the present embodiment will be described. FIG. 12 is a plan view illustrating a configuration of the present modification. FIG. 13 is a cross-sectional view taken along the line C-C of FIG. 12.

In a biomolecule analysis kit 1C of the present modification, reaction and detection can occur and be conducted in a region A1 which is located between the injection port 8 and the discharge port 9 so as not to overlap the waste liquid vessel 31 of the base 3 in the thickness direction. The region A1 includes a region where fluorescence, luminescence, color development, or the like can be detected from the lower side (lower surface) of the base 3 in the thickness direction (direction indicated by the reference sign D1 in FIG. 13), or from the upper side (top surface) of the base 3 in the thickness direction (direction indicated by the reference sign D2 in FIG. 13).

In the present modification, fluorescence, luminescence, color development, or the like in the microporous array layer 5 can be detected without the influence of the presence/absence of waste liquid or the amount of waste liquid.

It should be noted that various liquids may be injected from the discharge port 9, and surplus liquids may be discharged from the injection port 8 instead.

(Modification 6)

Figure 14:
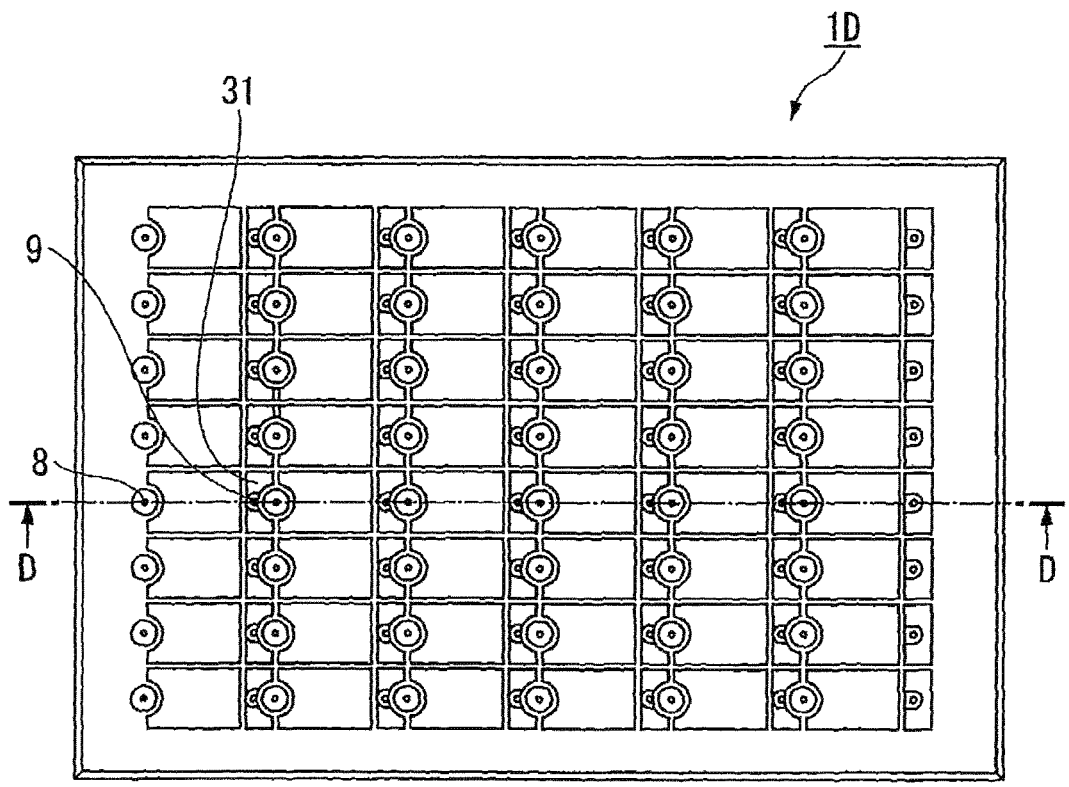
FIG. 14 is a plan view illustrating a configuration of still another modification (Modification 6) of the third embodiment.
Figure 15:
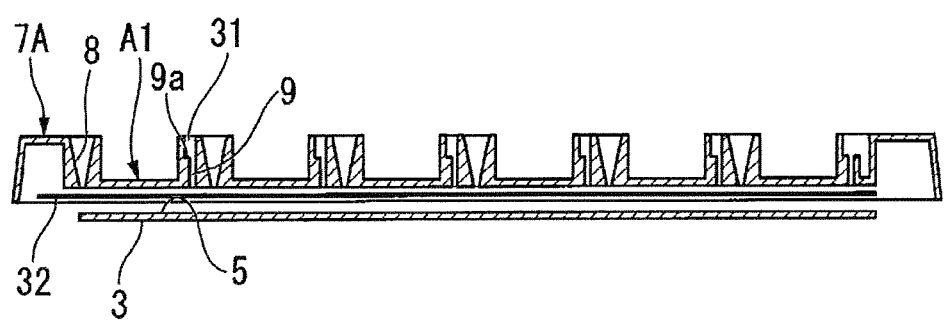
FIG. 15 is a cross-sectional view taken along the line D-D of FIG. 14.
Figure 16:
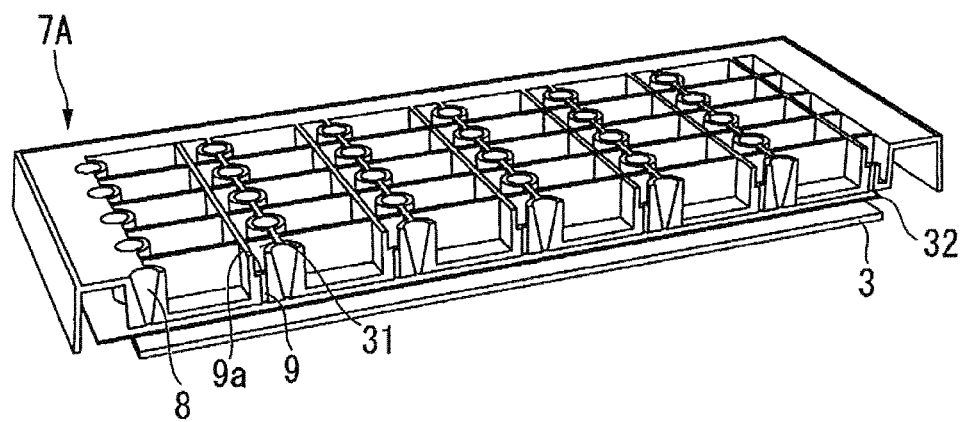
FIG. 16 is a perspective view illustrating a cross section taken along the line D-D of FIG. 14.
Figure 17:
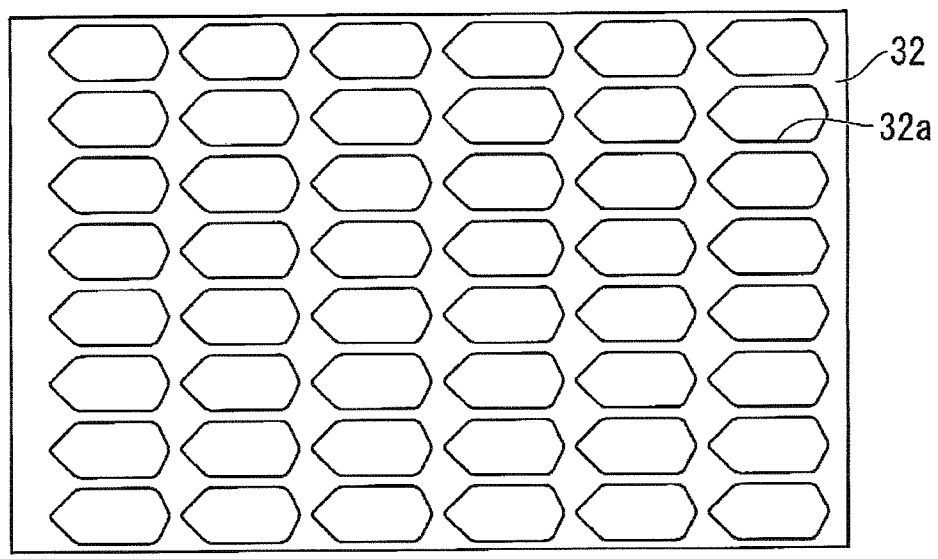
FIG. 17 is a plan view of illustrating a spacer member according to the modification (Modification 6).
Figure 18A:
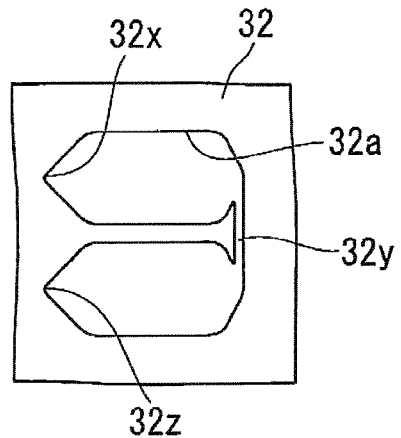
FIG. 18A is a plan view illustrating another configuration of the spacer member.
Figure 18B:
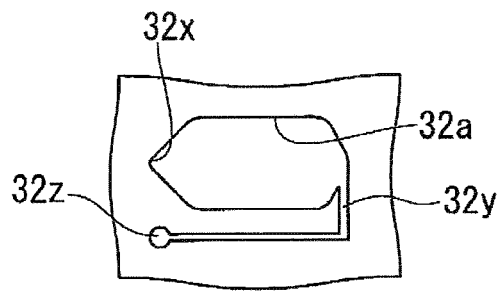
FIG. 18B is a plan view illustrating another configuration of the spacer member.
Figure 18C:
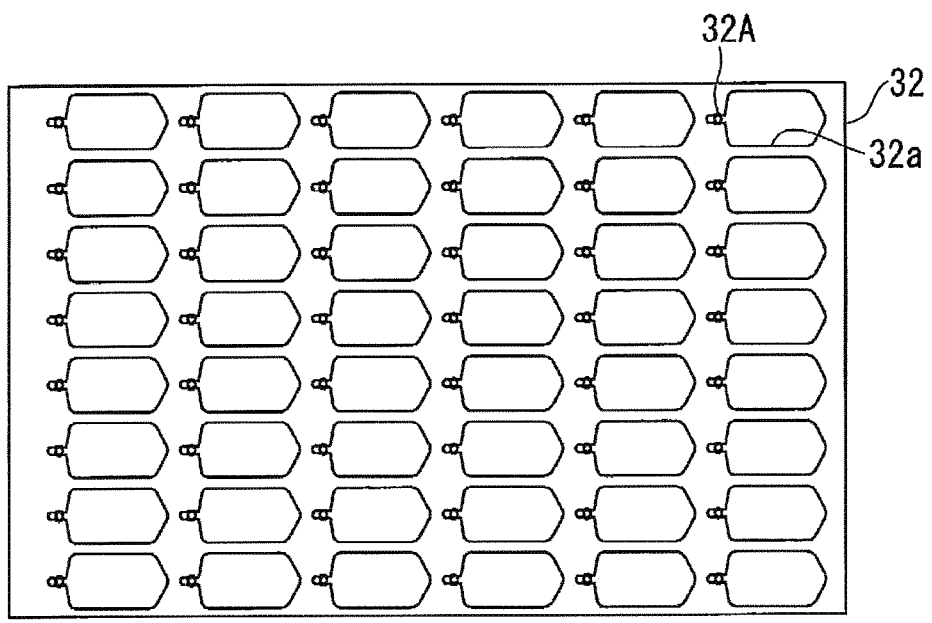
FIG. 18C is a plan view illustrating another configuration of the spacer member.
Figure 19:
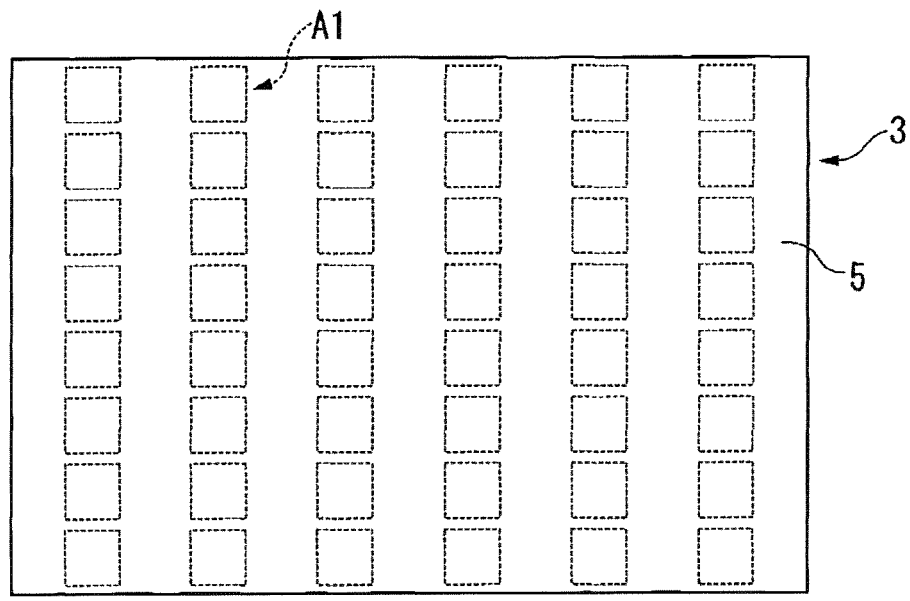
FIG. 19 is a plan view illustrating a base including a microporous array layer according to another modification (Modification 6) of the third embodiment.

Modification 6 of the present embodiment will be described. FIG. 14 is a plan view illustrating a configuration of the present modification. FIG. 15 is a cross-sectional view taken along the line D-D of FIG. 14. FIG. 16 is a perspective view illustrating a cross section taken along the line D-D of FIG. 14. FIG. 17 is a plan view illustrating a spacer member 32 of the present modification. FIGS. 18A, 18B, and 18C are plan views illustrating other configurations of the spacer member 32. FIG. 19 is a plan view illustrating the base 3 provided with a microporous array layer 5 of the present modification.

As shown in FIGS. 14 to 16, a biomolecule analysis kit 1D of the present modification includes a region A1 which is located between the injection port 8 and the discharge port 9 so as not to overlap the waste liquid vessel 31 of the base 3 in the thickness direction. Thus, similarly to Modification 5, fluorescence, luminescence, color development, or the like in the microporous array layer 5 can be detected without the influence of the presence/absence of waste liquid, or the influence of the amount of waste liquid.

In the present modification, since the injection port 8 is formed in a funnel shape, a pipette tip or the like, for injecting a liquid can be smoothly guided to the injection port 8. The injection port 8 may be located at the center of each well of an existing 96-well plate. Specifically, in the present modification, the injection port 8 may be disposed at 48 locations among the centers (96 locations) of the wells of the 96-well plate. Thus, the present modification can easily cope with the dispensing operation of existing ELISA devices.

Similarly to Modification 1, the discharge port 9 connected to the waste liquid vessel 31 is formed so that the waste liquid vessel side opening end 9*a* of the discharge port 9 is at a level higher than the level of the bottom surface of the waste liquid vessel 31.

As shown in FIG. 17, the spacer member 32 forms a gap that connects the injection port 8 to the discharge port 9 as shown in FIG. 15 to reserve a liquid, such as a reagent, between the injection port 8 and the discharge port 9.

As shown in FIGS. 18A and 18B, the structure of the spacer member 32 is not limited to the structure shown in FIG. 17 as long as the spacer member 32 includes an entrance 32*x* at a position aligning with the position of the injection port 8, an exit 32*z* at a position aligning with the position of the discharge port 9, and a channel 32*y* connecting the entrance 32*x* to the exit 32*z*.

For example, in the configuration shown in FIG. 18A as another configuration example of the spacer member 32, the channel 32*y* is provided to connect two regions A1 not overlapping the waste liquid vessel 31 (see FIG. 19).

For example, in the configuration shown in FIG. 18B as another configuration example of the spacer member 32, the entrance 32*x* and one end of the channel 32*y* at the position opposite to the entrance 32*x* are provided sandwiching the region A1 (see FIG. 19) that does not overlap the waste liquid vessel 31, while the other end of the channel 32*y* is routed to the entrance 32*x* side to bring the exit 32*z* to a position near the entrance 32*x*.

As shown in FIG. 18C, in the spacer member 32, a recess 32A may be formed near the injection port 8 to hold a solid reagent. Such recesses may hold various reagents that should be mixed immediately before detection. A liquid, such as a reagent, is passed via the injection port 8 to cause the reagents held in the recesses to dissolve into the liquid to thereby produce reactions.

In the present modification, a reaction, such as fluorescence, color development, or luminescence, can be detected in the region A1 having a substantially rectangular shape, located between the injection port 8 and the discharge port 9 (see FIG. 15).

As shown in FIGS. 14 and 19, in the present modification, reactions different from each other can be conducted at a maximum of 48 locations in the microporous array layer 5. The upper limit of the locations used for reactions different from each other in the microporous array layer 5 is not limited to 48.

The shapes of the cover 7A and the spacer member 32 are not limited to the shapes described above.

Figure 20:
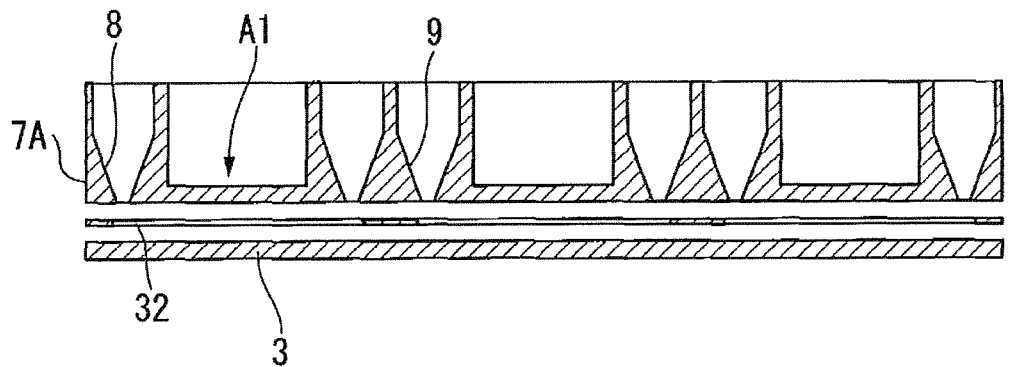
FIG. 20 is a cross-sectional view illustrating a configuration example of another modification of the modification (Modification 6).
Figure 21:
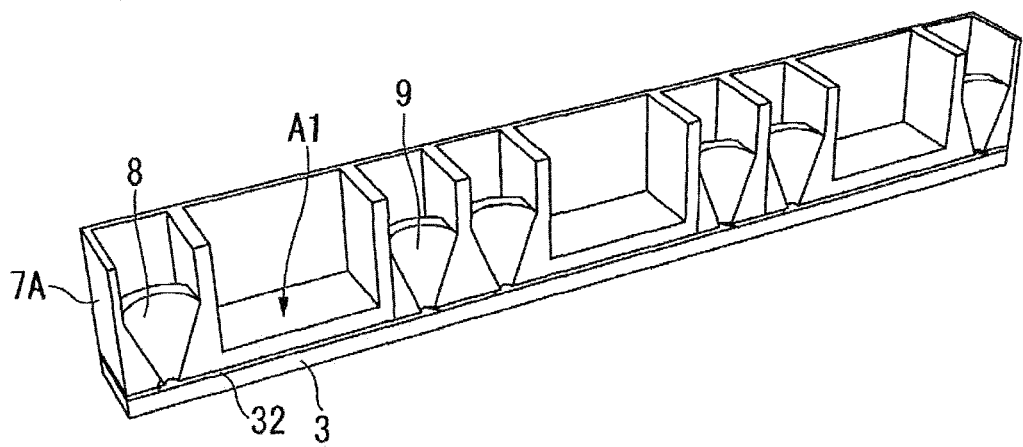
FIG. 21 is a perspective view illustrating the configuration example.
Figure 22:
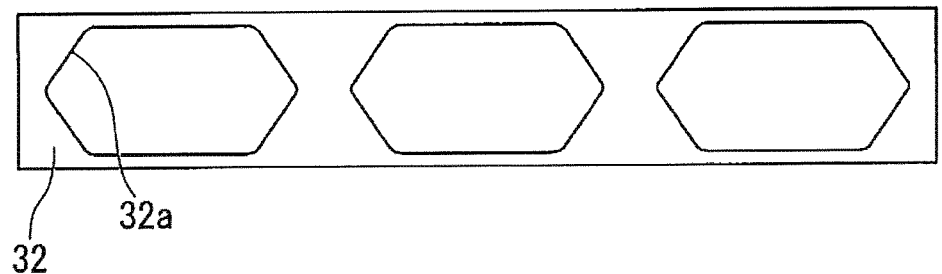
FIG. 22 is a plan view illustrating a spacer member of the configuration example.

For example, as shown in FIGS. 20 to 22, the injection port 8 and the discharge port 9 may be both in a funnel shape.

Figure 23:
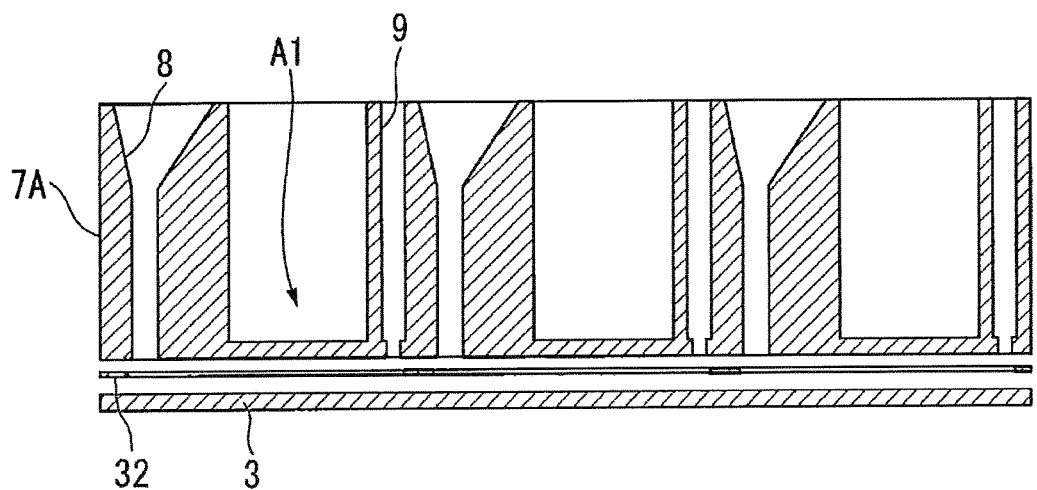
FIG. 23 is a cross-sectional view illustrating still another configuration example of the modification.
Figure 24:
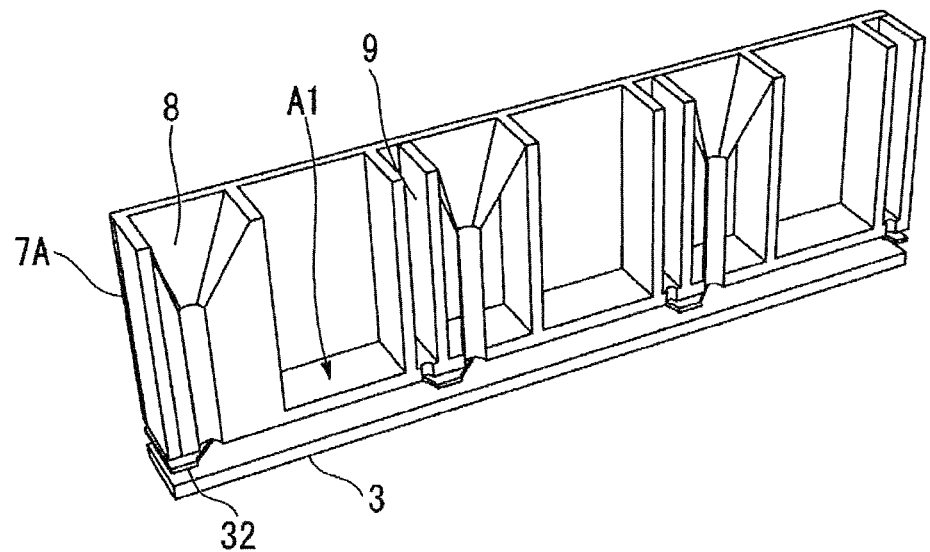
FIG. 24 is a perspective view illustrating the configuration example.

As shown in FIGS. 23 and 24, it may be so configured that the inner surface of the injection port 8 is formed of a plurality of planes, and the injection port 8 is tapered being gradually narrowed toward the base 3 (with the diameter of the injection port 8 being reduced).

It should be noted that various liquids may be injected from the discharge port 9 and the excess liquids may be discharged from the injection port 8 instead.

(Modification 7)

Figure 25:
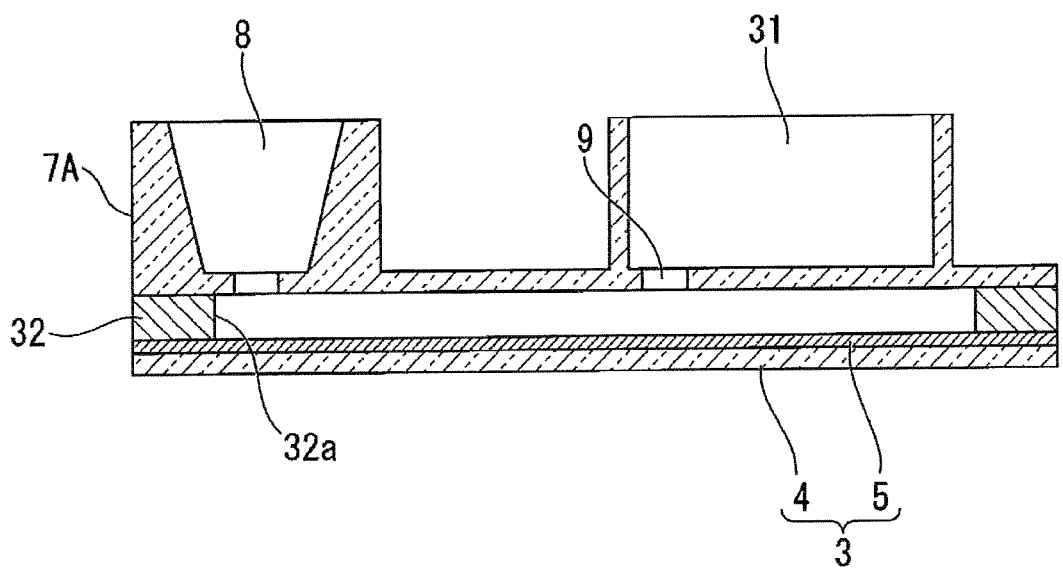
FIG. 25 is a cross-sectional view illustrating a configuration of still another modification (Modification 7) of the third embodiment.

Modification 7 of the present embodiment will be described. FIG. 25 is a cross-sectional view illustrating a configuration of the present modification.

As shown in FIG. 25, in the present modification, the injection port 8 is in a funnel shape. The interior of the injection port 8 is configured to be relatively large so that liquids do not remain in the injection port 8 due to capillary action. In the present modification, by dropping a liquid, such as a reagent, into the injection port 8, the liquid is delivered by its own weight.

For example, after a liquid containing a detection target, a reagent, and the like is delivered by the own weight of the liquid via the injection port 8, an oil having a specific gravity higher than that of the liquid is laid over the injection port 8. Then, the oil flows from the injection port 8 to the discharge port 9 by its own weight, during which each well 6 of the microporous array layer 5 (see the first embodiment) is individually sealed.

In the present modification, when the specific gravity of the liquid containing a detection target, a reagent, and the like is substantially 1, the specific gravity of the oil may be about 1.8, for example.

(Modification 8)

Figure 26:
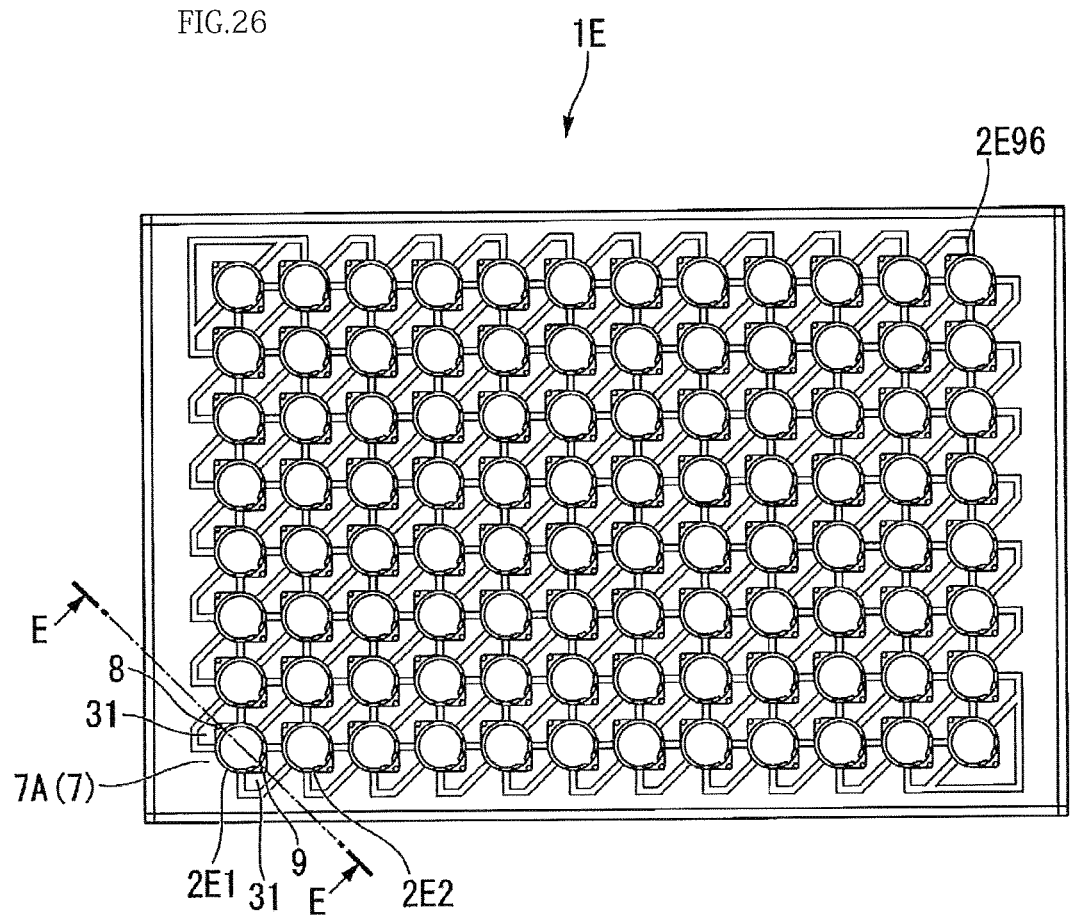
FIG. 26 is a plan view illustrating a configuration of still another modification (Modification 8) of the third embodiment.
Figure 27:
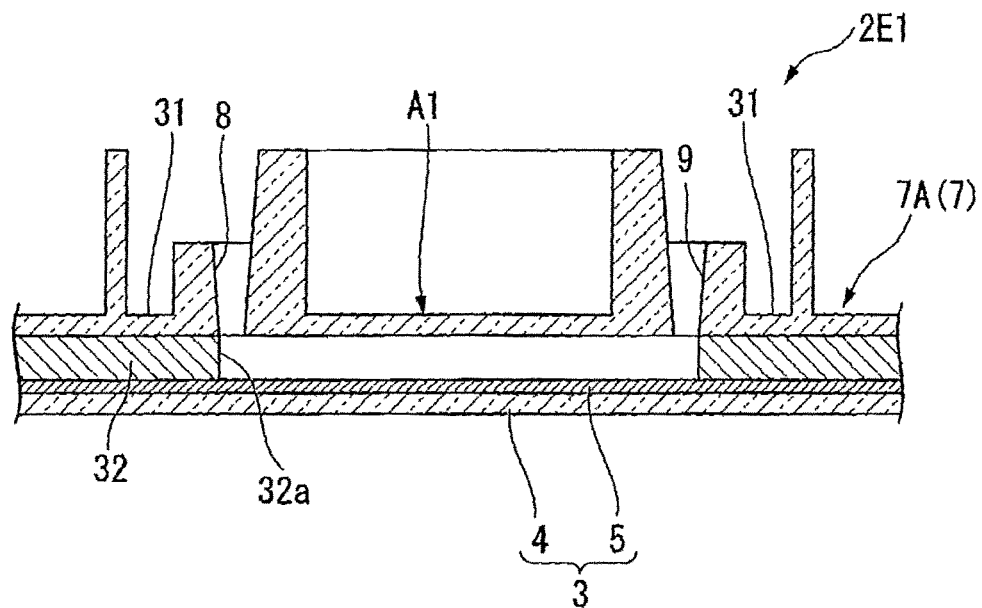
FIG. 27 is a cross-sectional view taken along the line E-E of FIG. 26.

Modification 8 of the present embodiment will be described. FIG. 26 is a plan view illustrating a configuration of the present modification. FIG. 27 is a cross-sectional view taken along the line E-E of FIG. 26.

As shown in FIGS. 26 and 27, in a biomolecule analysis kit 1E of the present modification, the waste liquid vessel 31 is formed on the injection port 8 side as well. The waste liquid vessel 31 formed on the injection port 8 side can collect liquid that overflows from the injection port 8 when the liquid is delivered from the discharge port 9 to the injection port 8 side.

The present modification can be used in such a way that a liquid containing a detection target, a reagent, and the like is delivered from the injection port 8, and then an oil is delivered from the discharge port 9. When the oil is delivered from the discharge port 9, the reagent and the oil overflowing from the injection port 8 are collected in the waste liquid vessel 31 on the injection port 8 side. The liquid collected in the waste liquid vessel 31 on the injection port 8 side is not mixed with the liquid collected in the waste liquid vessel 31 on the discharge port 9 side.

It should be noted that various liquids may be injected from the discharge port 9 and surplus liquids may be discharged from the injection port 8 instead.

(Modification 9)

Figure 28:
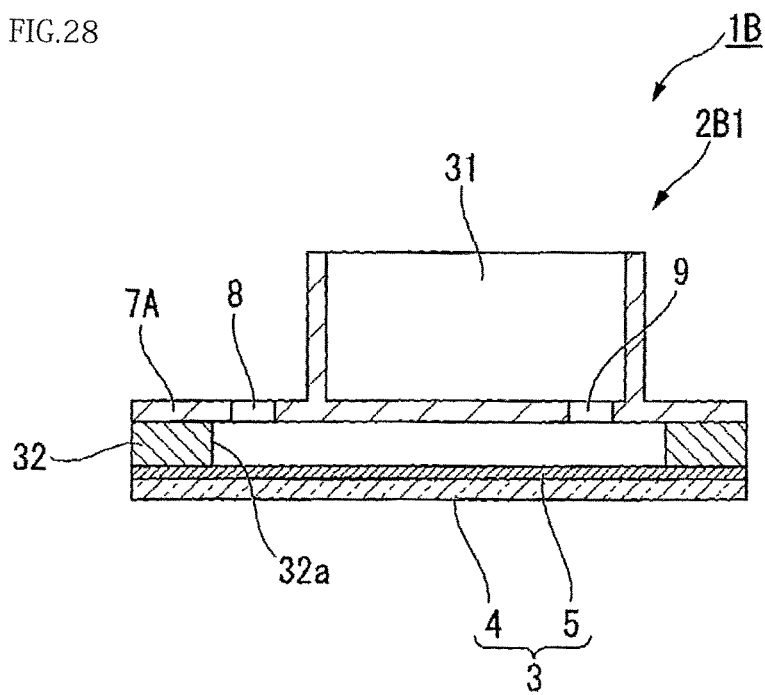
FIG. 28 is a cross-sectional view illustrating a configuration of still another modification (Modification 9) of the third embodiment.

Modification 9 of the present embodiment will be described. FIG. 28 is a cross-sectional view illustrating a configuration of the present modification.

As shown in FIG. 28, the present modification is different from the biomolecule analysis kit 1B of the third embodiment in that the cover 7A is made of a non-transmissive material. In this case, when fluorescence, luminescence, or color development is detected from the lower side of the base 3 in the thickness direction, there is substantially no influence from the waste liquid collected in the waste liquid vessel 31.

In the present modification, the cover 7A may be made of a material that is selectively non-transmissive to light of a specific wavelength. Being non-transmissive of the present modification may mean that light of a specific wavelength is absorbed, or may mean that light of a specific wavelength is reflected. For example, the cover 7A may be configured to be transmissive to visible light and non-transmissive to ultraviolet light. In this case, the cover 7A transmits excitation light for detecting fluorescence, but does not transmit fluorescence caused by the excitation light. As a result, when excitation light is irradiated from the lower side (lower surface) in the thickness direction of the base 3 and fluorescence is observed from the lower side (lower surface), the observation is hardly disturbed by the liquid in the waste liquid vessel 31, and the bright field created by the visible light transmitted through the cover 7A can be used as illumination light during the observation.

(Modification 10)

Figure 29:
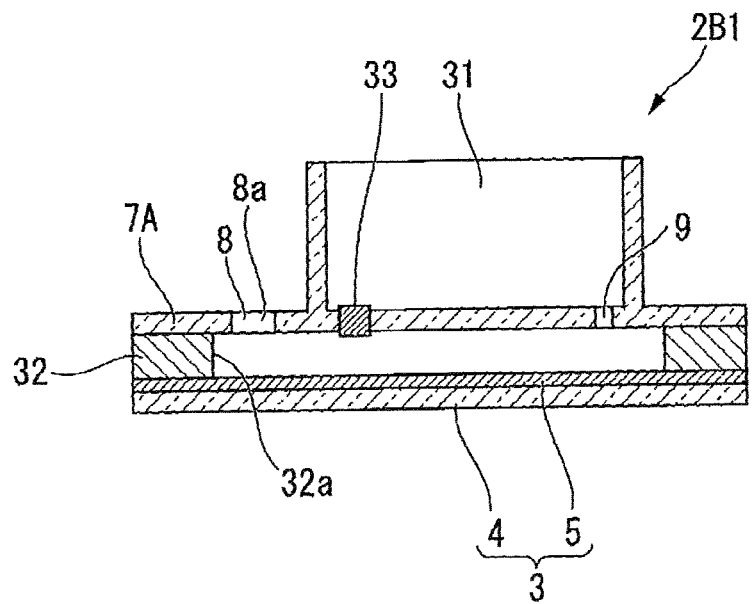
FIG. 29 is a cross-sectional view illustrating a configuration of still another modification (Modification 10) of the third embodiment.

Modification 10 of the present embodiment will be described. FIG. 29 is a cross-sectional view illustrating a configuration of the present modification.

As shown in FIG. 29, in the present modification, the cover 7A includes a filter 33 for causing air bubbles entering between the microporous array layer 5 and the cover 7A to move to the outside of the cover 7A. The filter 33 has a structure of transmitting gases but not liquids.

Similarly to the third embodiment, the present modification is provided with the injection port 8 and the discharge port 9.

In the present modification, the filter 33 provided in the cover 7A is disposed downstream of and in the vicinity of the injection port 8. Thus, air bubbles mixed in a reagent, an oil or the like are caught by the filter 33 before reaching the region of the microporous array layer 5 used for detection.

(Modification 11)

Figure 30:
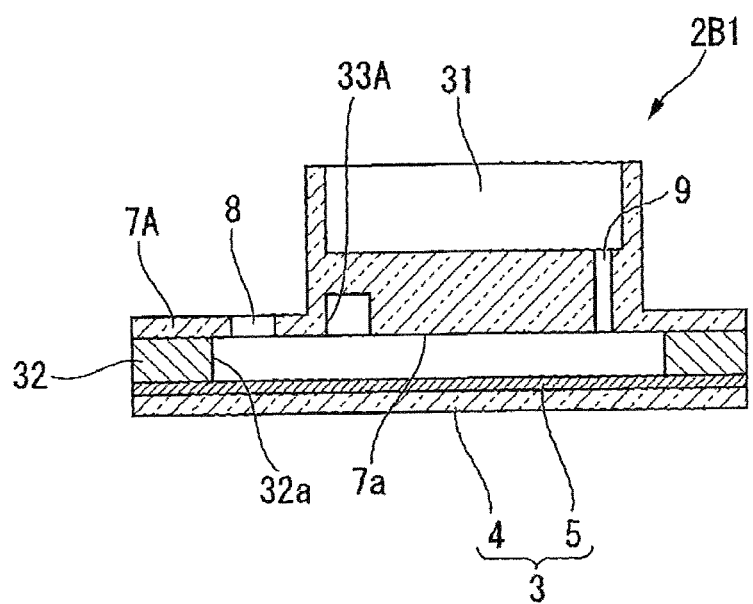
FIG. 30 is a cross-sectional view illustrating a configuration of still another modification (Modification 11) of the third embodiment.

Modification 11 of the present embodiment will be described. FIG. 30 is a cross-sectional view illustrating a configuration of the present modification.

In the present modification, instead of the filter 33 of Modification 10, a recess 33A for collecting air bubbles is formed in the cover 7A.

Similarly to Modification 10, the recess 33A formed in the cover 7A is preferably located downstream of and in the vicinity of the injection port 8. With this configuration as well, advantageous effects similarly to those of Modification 10 are achieved.

The present modification can efficiently catch larger air bubbles than in the case of providing the filter 33 of Modification 10.

(Modification 12)

Figure 31:
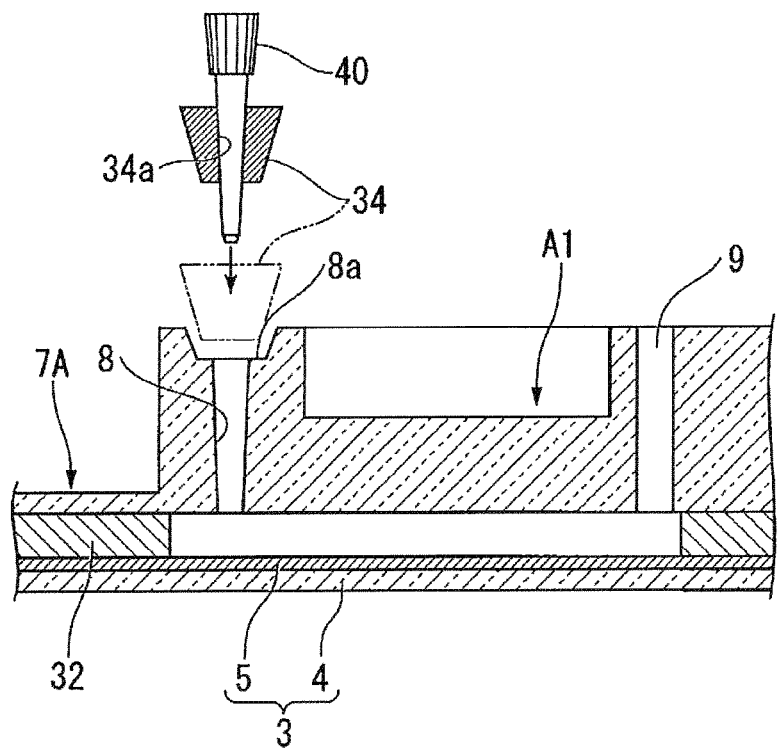
FIG. 31 is a cross-sectional view illustrating a configuration of still another modification (Modification 12) of the third embodiment.

Modification 12 of the present embodiment will be described. FIG. 31 is a cross-sectional view illustrating a configuration of the present modification.

The present modification includes an adapter 34 in contact with the injection port opening end 8a of the injection port 8 and formed with a through hole 34a through which a pipette tip 40 is inserted into the injection port 8.

The adapter 34 is used being combined with the pipette tip 40 which is used for the delivery of a reagent and an oil. The outer shape of the adapter 34 is not limited specifically. The outer shape of the adapter 34 of the present embodiment is a truncated cone shape with a diameter gradually reduced toward the pipette tip 40 when the pipette tip 40 is mounted to the adapter 34.

In the present modification, for example, when the adapter 34 is mounted to the pipette tip 40 and the tip end of the pipette tip 40 is inserted into the injection port 8, the adapter 34 comes into contact with the injection port opening end 8a. Thus, the cover 7A is pushed toward the base 3. As a result, the capacity of the gap between the cover 7A and the base 3 is reduced to cause the liquid between the cover 7A and the base 3 to leak from the injection port 8 and the discharge port 9 in small amounts. During the leakage, air bubbles, if present near the injection port opening end 8a of the injection port 8, are expelled from the injection port opening end 8a. Accordingly, in the delivery of the reagent or oil from the pipette tip 40, the air bubbles near the injection port opening end 8a are prevented from being delivered.

(Modification 13)

Figure 32A:
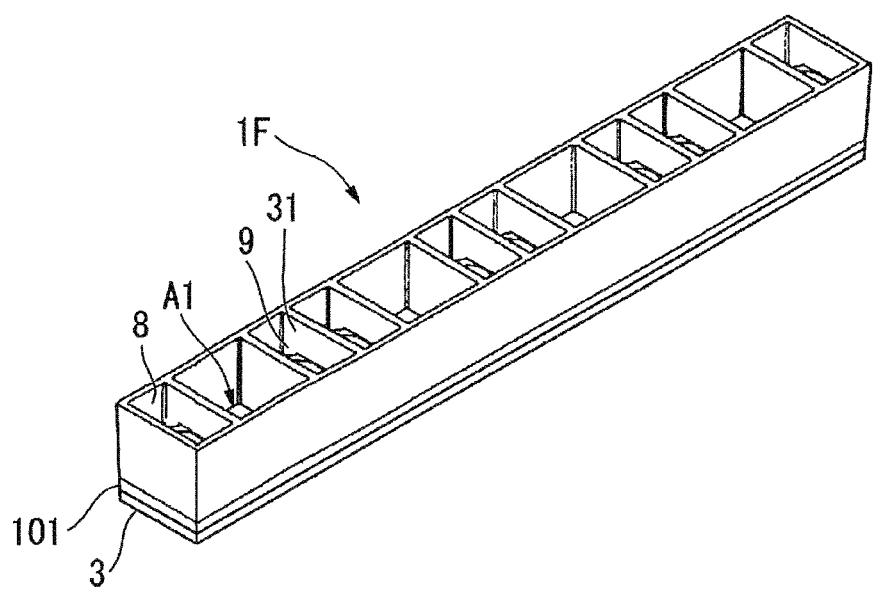
FIG. 32A is a perspective view illustrating a configuration of still another modification (Modification 13) of the third embodiment.
Figure 32B:
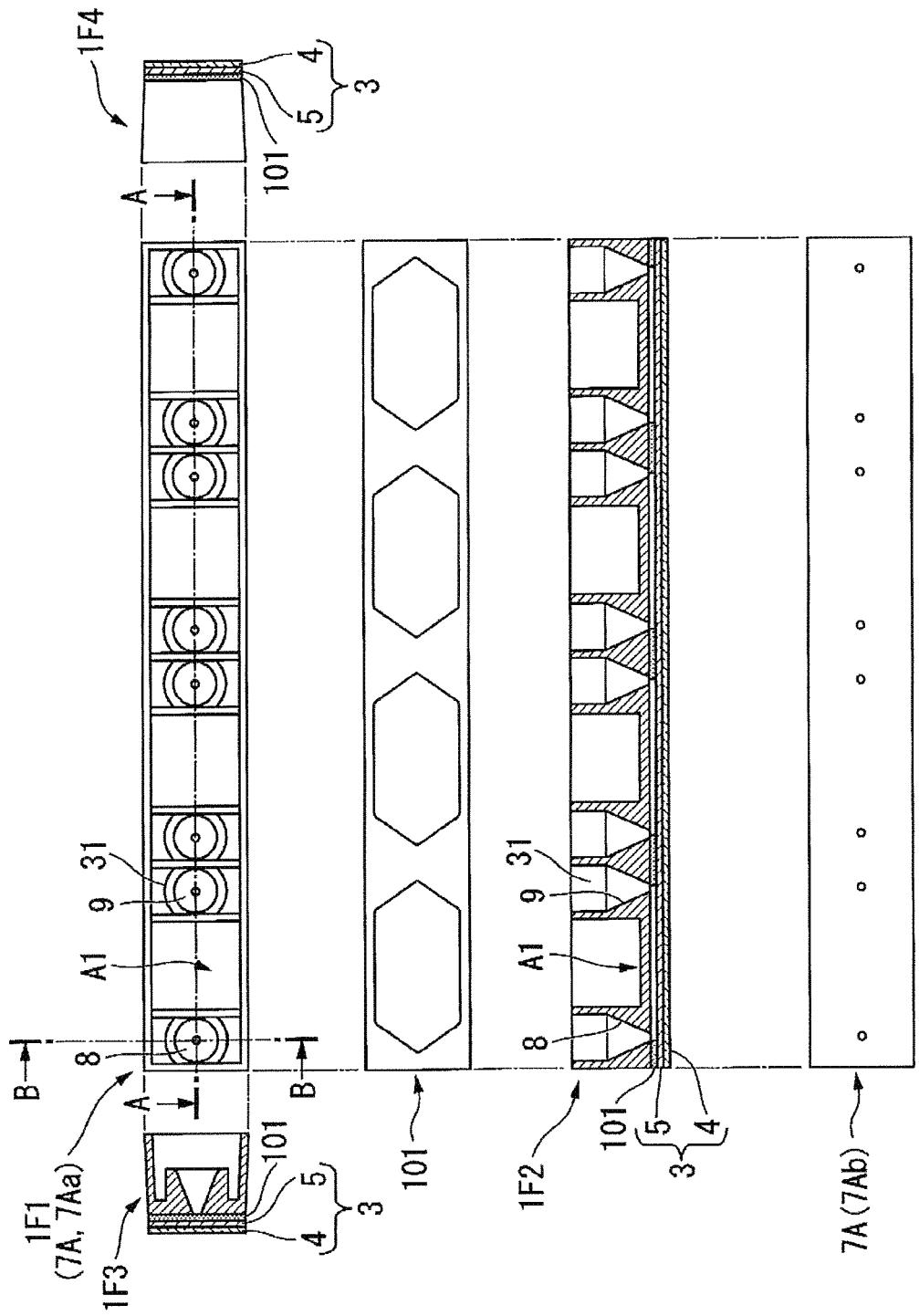
FIG. 32B is a six-sided view illustrating a configuration of still another modification (Modification 13) of the third embodiment.

Modification 13 of the present embodiment of the present invention will be described. FIG. 32A is a perspective view illustrating a configuration of a biomolecule analysis kit 1F of the present modification. FIG. 32B is a set of diagrams including a plan view 1F1 of the biomolecule analysis kit 1F (corresponding to a plan view 7Aa of the cover 7A), a cross-sectional view 1F2 taken along the line A-A, a cross-sectional view 1F3 taken along the line B-B, a side view 1F4, a plan view of a sealing member 101, and a bottom view 7Ab of the cover 7A.

As shown in FIGS. 32A and 32B, similarly to Modification 6, the biomolecule analysis kit 1F of the present modification is provided with a region A1 between the injection port 8 and the discharge port 9, in which the microporous array layer 5 is arranged so as not to overlap the waste liquid vessel 31 in the thickness direction of the base 3. Being provided with the region A1, fluorescence, luminescence, color development, or the like is detected in the microporous array layer 5 without being influenced by the presence/absence or the amount of the waste liquid.

In the present modification, the injection port 8 is formed in a funnel shape, so that a pipette tip or the like for injecting a liquid can be smoothly guided to the injection port 8.

As shown in FIGS. 32A and 32B, similarly to the injection port 8, the discharge port 9 connected to the waste liquid vessel 31 of the present modification is in a funnel shape to smoothly guide the pipette tip or the like to the discharge port 9.

Similarly to Modification 8, the present modification can be used in such a way that a liquid containing a detection target, a reagent, and the like is delivered from the injection port 8, and then an oil is delivered from the discharge port 9.

After injection of the liquid containing a detection target, a reagent, and the like from the injection port 8, the liquid flows from the gap between the cover 7A and the base 3 into the waste liquid vessel 31 via the discharge port 9. Since the liquid is present around the waste liquid vessel 31 and the discharge port 9, air is unlikely to mix with the liquid in the gap between the cover 7A and the base 3 in injecting the oil from the discharge port 9 using a pipette or the like.

In other words, the present modification can easily prevent mixing of air when injecting an oil into the liquid in the gap between the cover 7A and the base 3.

Thus, the present modification can reduce the probability of air bubbles entering the liquid filled in the gap between the cover 7A and the base 3 in delivering the liquid. Accordingly, highly accurate quantitative analysis can be conducted with simple and easy manipulation.

As shown in FIG. 32B, similarly to the spacer member 32 of other modifications, the sealing member 101 connects the injection port 8 to the discharge port 9 shown in FIG. 32B and forms a gap therebetween for the liquid, such as a reagent, to remain.

Similarly to the spacer member 32 shown in FIGS. 18A and 18B, the structure of the sealing member 101 is not limited to the structure shown in FIG. 32B as long as the sealing member 101 includes an entrance positionally aligning with the injection port 8, an exit positionally aligning with the discharge port 9, and a channel connecting the entrance to the exit.

In the present modification, a reaction of fluorescence, color development, or luminescence can be detected in the substantially rectangular region A1 located between the injection port 8 and the discharge port 9 (see FIG. 32B).

In the line kit shown in FIGS. 32A and 32B, one injection port 8, one region A1, one discharge port 9, and one waste liquid vessel 31 may be used as one unit. In other words, the biomolecule analysis kit 1F of the present modification may be used as a line kit, or may be used as an analysis kit segment by cutting and separating the line kit on a single-unit basis.

FIG. 32A shows a single-row type line kit. However, as shown in other modifications, the biomolecule analysis kit 1F of the present modification may be formed as a 96-hole type kit. In this case, the injection port 8 may be located at the center of each well of an existing 96-well plate. Specifically, in the present modification, the injection port 8 may be located at 48 locations among the centers (96 locations) of the wells of the 96-well plate. Thus, the present modification can easily cope with the dispensing operation of existing ELISA devices.

FIG. 32B shows a configuration in which the sealing member 101 is provided separately from the base 3 made up of the substrate 4 and the microporous array layer 5. However, the sealing member 101 and the base 3 may be integrally formed.

(Modification 14)

Figure 33A:
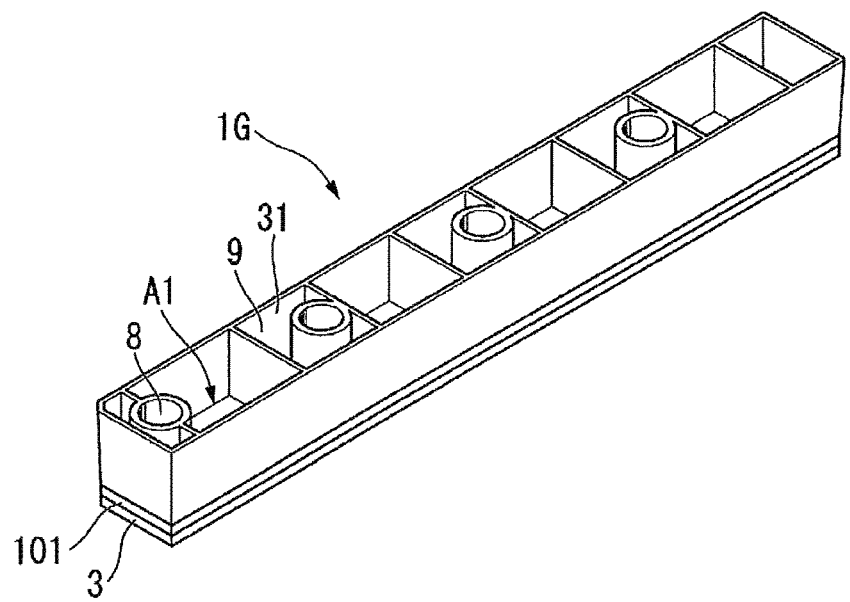
FIG. 33A is a perspective view illustrating a configuration of still another modification (Modification 14) of the third embodiment.

Modification 14 according to the present embodiment of the present invention will be described. FIG. 33A is a perspective view illustrating a configuration of a biomolecule analysis kit 1G of the present modification. FIG. 33B is a set of diagrams including a plan view 1G1 of the biomolecule analysis kit 1G (corresponding to a plan view 7Aa of the cover 7A), a cross-sectional view 1G2 taken along the line A-A, a left side view 1G3, a right side view 1G4, a plan view of the sealing member 101, and a bottom view 7Ab of the cover 7A.

As shown in FIGS. 33A and 33B, similarly to Modification 6, the biomolecule analysis kit 1G of the present modification is provided with the region A1 between the injection port 8 and the discharge port 9. In the region A1, the microporous array layer 5 is disposed so as not to overlap the waste liquid vessel 31 in the thickness direction of the base 3. Being provided with the region A1, fluorescence, luminescence, color development, or the like in the microporous array layer 5 can be detected without being influenced by the presence/absence or the amount of the waste liquid.

In the present modification, the injection port 8 is formed in a funnel shape, so that a pipette tip or the like for injecting a liquid can be smoothly guided to the injection port 8.

As shown in FIG. 33B, in the present modification, when the base 3 is defined to be on a lower side and the cover 7A is defined to be on an upper side in the thickness direction of the base 3, the level of the injection port opening end 8a of the injection port 8 is lower than the level of the waste liquid vessel side opening end 9a of the discharge port 9. Moreover, the waste liquid vessel side opening end 9a of the discharge port 9 is at a level higher than the bottom surface of the waste liquid vessel 31.

In the present modification, various liquids are permitted to flow in from the injection port opening end 8a before the liquids enter the waste liquid vessel 31 from the waste liquid vessel side opening end 9a of the discharge port 9. Then, when the injection port opening end 8a is opened, the gravity causes the liquid level in the injection port 8 to equalize with that of the discharge port 9, during which the liquids flow back from the injection port opening end 8a with the liquid amount in the discharge port 9 being the upper limit. Thus, air bubbles, if present near the injection port opening end 8a, are swept away by the backflow liquids, and expelled from the injection port opening end 8a. In the present modification, air bubbles are unlikely to remain in the gap between the base 3 and the cover 7A, in the vicinity of the injection port 8.

In the present modification, the waste liquid vessel side opening end 9a of the discharge port 9 is at a level higher than the bottom surface of the waste liquid vessel 31. Thus, the liquids that have entered the waste liquid vessel 31 are unlikely to flow back into the gap between the base 3 and the cover 7A via the discharge port 9.

In the biomolecule analysis kit 1G of the present modification, the waste liquid vessel 31 is formed so that the capacity of the waste liquid vessel 31 is greater than the sum injection amount of the reagent and oil. Thus, in injecting the reagent and oil, the liquid is unlikely to leak from the waste liquid vessel 31 to the outside of the biomolecule analysis kit 1G.

As shown in FIG. 33B, similarly to Modification 13, the sealing member 101 connects between the injection port 8 and the discharge port 9 shown in FIG. 33B, and forms a gap therebetween for the liquid, such as a reagent, to remain.

Similarly to Modification 13, the structure of the sealing member 101 is not limited to the structure shown in FIG. 33B as long as the sealing member 101 includes an entrance positionally aligning with the injection port 8, a discharge port positionally aligning with the discharge port 9, and a channel connecting the injection port to the discharge port.

In the present modification, a reaction of fluorescence, color development, or luminescence can be detected in the substantially rectangular region A1 located between the injection port 8 and the discharge port 9 (see FIG. 33B).

In the line kit shown in FIGS. 33A and 33B, one injection port 8, one region A1, one discharge port 9, and one waste liquid vessel 31 may be used as one unit. In other words, the biomolecule analysis kit 1G of the present modification may be used as a line kit, or may be used as an analysis kit segment by cutting and separating the line kit on a single-unit basis.

FIG. 33A shows a one-row type line kit. However, as shown in other modifications, the analysis kit of the present modification may be formed as a 96-hole type kit. In this case, the injection port 8 may be located at the center of each well of an existing 96-well plate. Specifically, in the present modification, the injection port 8 may be located at 48 locations among the centers (96 locations) of the wells of the 96-well plate. Thus, the present modification can easily cope with the dispensing operation of existing ELISA devices.

FIG. 33B shows a configuration in which the sealing member 101 is provided separately from the base 3 formed of the substrate 4 and the microporous array layer 5. However, the sealing member 101 and the base 3 may be integrally formed.

(Modification 15)

Modification 15 according to the present embodiment of the present invention will be described.

Modifications 13 and 14 show the use of the line kit by cutting the kit on a one-unit basis. However, the base 3 and the sealing member 101 may be integrally formed into a beaker- or tubular-shaped vessel 103.

Being formed with no channel, this configuration enables introduction of biomolecules 102, such as nucleic acids, into the wells 6, and also enables detection, with the liquid being filled in the batch vessel 103.

The vessel 103 may be provided with a plurality of wells 6.

Also, when adopting a batch-type vessel 103, the aqueous solution 10 may be filled in the wells 6 beforehand during manufacture, so that the biomolecules 102, such as nucleic acids as a detection target, are diffused in the wells 6 and the biomolecules 102 are introduced into the wells 6 and are ready for detection by the time the kit user conducts analysis tests in situ.

If the aqueous solution 10 is not filled in the wells 6 beforehand during manufacture, it is difficult to degas the wells 6 for the removal of air bubbles, when the kit user conducts analysis tests in situ.

Thus, in the present modification, the aqueous solution 10 is preferably filled in the wells 6 beforehand during manufacture.

In the present modification, introduction of biomolecules and analysis thereof, including detection and observation can be conducted similarly to the foregoing embodiments.

The biomolecule introduction method has been described in the foregoing embodiments by way of an example of a method of introducing nucleic acids. However, the biomolecules to be introduced using the method may be DNA, RNA, miRNA, mRNA, proteins, exosomes, liposomes, cells, or the like.

The biomolecule introduction method of the present embodiment can be conducted similarly to the foregoing nucleic acid introduction methods, and biomolecules are not limited only to nucleic acids.

Similarly, the nucleic acid detection method, the biomolecule analysis method, the array device for biomolecule quantification, and the biomolecule analysis kit of the foregoing embodiments may use as a target biomolecules including DNA, RNA, miRNA, mRNA, proteins, exosomes, cells, or the like. Analysis targets are not limited to ones shown in the foregoing embodiments.

Example

Hereinafter, the nucleic acid introduction method (the biomolecule introduction method), the biomolecule analysis method, the array device 2 for nucleic acid quantification, and the biomolecule analysis kit 1 according to the embodiments of the present invention will be described in detail by way of an example. The example below, that is a specific example to which the present invention is applied, should not limit the present invention.

<Preparation of Array Device for Nucleic Acid Quantification>

CYTOP (registered trademark) (manufactured by Asahi Glass Co., Ltd) that is a hydrophobic resin was spin-coated on a glass substrate 4 having a thickness of 0.5 mm, followed by thermosetting at 180° C. for hours. The thermoset substrate was then subjected to photolithography to prepare a base 3 with 1,000,000 pores, each having a 5 µm-diameter. The layer formed on the substrate 4 by spin coating CYTOP (registered trademark) was formed into a shape by photolithography, thereby forming the microporous array layer 5 disclosed in the embodiments described above. The layer formed on the substrate 4 by spin coating CYTOP (registered trademark) had a thickness of 3 µm.

Subsequently, a cover glass was placed on the base 3 as the cover 7 so that the gap between the base 3 and the cover 7 was 100 µm. A spacer that was an adhesive tape was disposed between the base 3 and the cover 7. Moreover, an aqueous liquid, as a replacement solution, containing no nucleic acid was delivered between the base 3 and the cover 7 to entirely fill the 5 µm-diameter pores and the gap between the base 3 and the cover 7. The aqueous liquid of the present example had a composition of 20 µM MOPS pH 7.5, 15 mM NaCl, and 6.25 mM $MgCl_2$.

\<Delivery of Mixed Solution of Sample and Detection Reaction Reagent\>

An Invader reaction reagent (2 µM allele probe, 1 µM Invader oligo, 1 µM FAM labeled arm, 20 µM MOPS pH 7.5, 15 mM NaCl, 6.25 mM $MgCl_2$, and 50 U/µL of Cleavase (registered trademark)) was mixed with a synthetic DNA, and the resultant mixed solution X was delivered to the gap between the base 3 and the cover 7. The synthetic DNA in this case was added to the mixed solution X at a concentration of 30 µM so that 1 molecule of the synthetic DNA is trapped by each of the 5 µm-diameter pores formed in the base 3.

The columnar micropore with a diameter of 5 µm had a height of 3 µm and a volume of 59 fL. According to the Poisson distribution, the synthetic DNA at the concentration of 30 µM was estimated to enter 65% of micropores among the 1,000,000 micropores. After delivery of the mixture of the Invader reaction reagent and the synthetic DNA, FC-40 (SIGMA) was delivered to the gap between the base 3 and the cover 7 as the oleaginous sealing liquid 12 to seal the 5 µm-diameter pores, thereby forming 1,000,000 independent nucleic acid detection reaction vessels 6A.

\<Measurement of Fluorescence Intensity\>

Subsequently, the array device 2 for nucleic acid quantification of the present example having the 1,000,000 independent nucleic acid detection reaction vessels 6A was incubated in an oven at 62° C., and removed 15 minutes later. Then, an image of the reaction vessels 6A was captured with a fluorescence microscope for observation of the fluorescence intensity of the pores. Herein, the image of the reaction vessels 6A after reaction was captured using a fluorescence microscope (Carl Zeiss, AX10), a light source (LEJ, FluoArc 001.26A usable with HBO 10), a sensor (Hamamatsu Photonics K.K., EM-CCD C9100), a filter (Olympus Corporation, U-MNIBA2), analysis software (Hamamatsu Photonics K.K., AQUACOSMOS 2.6, exposure time 488 ms, EM gain 120, offset 0, binning×1). The number of the reaction vessels 6A emitting fluorescence with sufficient S/N relative to autofluorescence was counted among the reaction vessels 6A.

Figure 34:
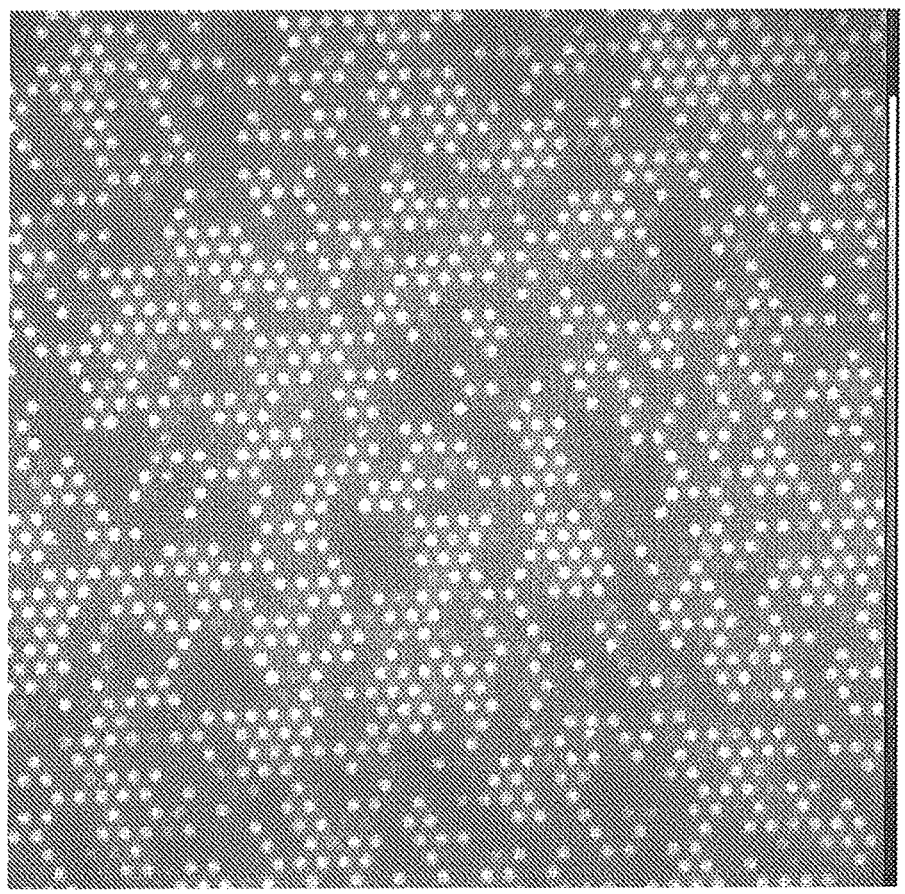
FIG. 34 is a photograph showing a result of biomolecule analysis according to an example of the present invention.

FIG. 34 is a photograph showing the results of biomolecule analysis of the present example. In the present example, as shown in FIG. 34, fluorescent luminescence due to Invader reaction was observed in about 65% reaction vessels 6A among the total number of the reaction vessels 6A. This is in agreement with the estimation based on the Poisson distribution, and shows that the Invader reaction reagent and the synthetic DNA were favorably trapped by the reaction vessels 6A for the progress of Invader reaction, and the measured results were in conformity with the concentration of the synthetic DNA.

In the techniques disclosed in Non-Patent Literatures 1 and 2, if air bubbles mingle in the wells, the air bubbles should be removed from the wells. Removal of the air bubbles involves complicated manipulation before conducting highly accurate quantitative analysis.

The present invention has an aspect of providing a nucleic acid introduction method (biomolecule introduction method) avoiding entry of air bubbles into the wells, a nucleic acid detection method enabling highly accurate quantitative analysis with simple and easy manipulation, a biomolecule analysis method, an array device for use in quantifying biomolecule nucleic acids, and a biomolecule analysis kit.

An array device for biomolecule quantification according to a first aspect of the present invention includes: a base having a plurality of wells, a cover having a gap between the base and the cover and laid over the base to cover openings of the plurality of wells, an injection port communicating with the gap between the base and the cover, and a discharge port formed at a position apart from the injection port and communicating with the gap between the base and the cover. In the device, after an aqueous solution is filled in between the base and the cover, a liquid containing biomolecules is introduced from the injection port into the gap between the base and the cover to discharge surplus aqueous solution, the surplus aqueous solution being outside the plurality of wells, from the discharge port, and the biomolecules are transferred by diffusion to the aqueous solution filled in the plurality of wells.

In the array device for biomolecule quantification, the device may include the aqueous solution filled in between the base and the cover.

In the array device for biomolecule quantification, at least either the plurality of wells or the cover may be light transmissive.

In the array device for biomolecule quantification, each of the plurality of wells includes an electrode, and the base may include a wire connected to the electrode, and a connector for connecting the wire to a detection circuit.

In the array device for biomolecule quantification, the device may include a region provided with the plurality of wells for a signal amplification reaction, the region being located not to overlap the injection port and the discharge port as viewed in a thickness direction of the base.

The array device for biomolecule quantification may further include a waste liquid vessel communicating with the discharge port and collecting liquid that flows in from the gap between the base and the cover via the discharge port.

In the array device for biomolecule quantification, the device may include a region provided with the plurality of wells for the signal amplification reaction, the region being located not to overlap the injection port, the waste liquid vessel and the discharge port as viewed from a thickness direction of the base.

A biomolecule analysis kit according to a second aspect of the present invention includes the array device for biomolecule quantification according to the above aspect, a detection reaction reagent for the biomolecules, and an oleaginous sealing liquid deliverable from the injection port into the gap between the base and the cover. In the biomolecule analysis kit, the aqueous solution is a buffer solution not containing nucleic acids.

A nucleic acid introduction method according to a third aspect of the present invention includes delivering a mixed solution containing a template nucleic acid into a channel in an array device for nucleic acid quantification, the device having a plurality of wells formed in the channel, the channel and the plurality of wells being filled with an aqueous solution, and diffusing the mixed solution delivered to the channel into the aqueous solution in the plurality of wells.

An oleaginous sealing liquid may be delivered into the channel to seal the mixed solution and the aqueous solution in the plurality of wells with the oleaginous sealing liquid to thereby provide the plurality of wells in the form of a plurality of independent nucleic acid detection reaction vessels.

The mixed solution may contain a signal amplification reaction reagent for a signal amplification reaction in the nucleic acid detection reaction vessels, and signal detection may be conducted in the nucleic acid detection reaction vessels.

The signal amplification reaction may be an enzymatic reaction.

The enzymatic reaction may be an isothermal reaction.

The enzymatic reaction may be an Invader reaction.

In the nucleic acid introduction method, the signal detection may be based on detection of at least one of fluorescence, luminescence, pH change, absorbance change, and electrical potential change according to presence/absence of the template nucleic acid in the nucleic acid detection reaction vessels.

A biomolecule analysis method according to a fourth aspect of the present invention is a biomolecule analysis method using the nucleic acid detection method according to the third aspect. In the biomolecule analysis method, the mixed solution contains any of DNA, RNA, miRNA, mRNA, or proteins to be an analysis target substance, and a labeling substance having a specific labeling function to the analysis target substance is contained in at least either the mixed solution or the aqueous solution in a state in which the template nucleic acid is contained in the labeling substance or the template nucleic acid is bondable to the labeling substance.

In the biomolecule analysis method, the labeling substance may contain at least one of a DNA chain, enzyme, particle, antibody, and liposome different from the template nucleic acid.

According to the aspects of the present invention, there can be provided a nucleic acid introduction method (biomolecule introduction method) with which air bubbles are unlikely to enter wells, a nucleic acid detection method that enables highly accurate quantitative analysis with simple and easy manipulation, a biomolecule analysis method, an array device for nucleic acid quantification, and a biomolecule analysis kit.

Several embodiments of the present invention have been described so far in detail with reference to the drawings and the example. Specific configurations are not limited to these embodiments, but include design changes or the like within a range not departing from the spirit of the present invention.

| Reference Signs List | |
| --- | --- |
| 1, 1A, 1B, 1C, 1D, 1E, 1F, 1G | Biomolecule analysis kit |
| 2, 2A, 2B1 to 2B96 | Array device for nucleic acid quantification |
| 3 | Base |
| 4 | Substrate |
| 4a | Substrate surface |
| 5 | Microporous array layer |
| 5a | Through hole |
| 6 | Well |
| 6a | Bottom part |
| 6A | Nucleic acid detection reaction vessel |
| 7, 7A | Cover |
| 8 | Injection port |
| 8a | Injection port opening end |
| 9 | Discharge port |
| 9a | Waste liquid vessel side opening end |
| 10 | Aqueous solution |
| 11 | Detection reaction reagent |
| 12 | Oleaginous sealing liquid |
| 20 | Electrode |
| 21 | Wire |
| 22 | Connector |
| 31 | Waste liquid vessel |
| 32 | Spacer member |
| 32a | Through hole |
| 33 | Filter |
| 34 | Adapter |
| 40 | Pipette tip |
| 101 | Dealing member |
| 102 | Biomolecule |
| 103 | Vessel |

Obviously, numerous modifications and variations of the present invention are possible in light of the above teachings. It is therefore to be understood that within the scope of the appended claims, the invention may be practiced otherwise than as specifically described herein.

What is claimed is:

1. An array kit device, comprising:
a base having a plurality of wells configured to be filled with an aqueous solution;
a cover positioned over the base and including a plurality of waste liquid vessels such that the cover covers openings of the wells and forms a gap forming a channel between the cover and the opening of the wells; and
a spacer member connecting the base and the cover such that the spacer member sections the gap into a plurality of watertight portions corresponding to the plurality of waste liquid vessels in the cover, respectively,
wherein the cover has a plurality of injection ports positioned to inject an oleaginous sealant into the plurality of watertight portions, respectively, and a plurality of discharge ports positioned apart from the plurality of injection ports respectively such that the plurality of discharge ports discharges surplus amounts of the aqueous solution in the plurality of watertight portions outside the wells by the oleaginous sealant injected into the plurality of watertight portions from the plurality of injection ports, each of the waste liquid vessels is formed on an opposite side of the gap and configured to collect the surplus amounts of the aqueous solution discharged from the plurality of watertight portions via the plurality of discharge ports respectively such that the plurality of waste liquid vessels is directly communicating with the plurality of discharge ports, respectively, and the cover is formed such that each of the discharge ports has an opening end formed on a respective waste liquid vessel side and is made of a material that is selectively non-transmissive to light in a specific wavelength range.

2. The array kit device of claim 1, wherein the plurality of injection ports and the plurality of discharge ports are configured such that when a liquid containing a biomolecule for analysis is injected into the plurality of watertight portions from the plurality of injection ports, the biomolecule diffuses to the aqueous solution filled in the wells and that the surplus amounts of the aqueous solution outside the wells are discharged from the plurality of discharge ports by the oleaginous sealant, respectively.

3. The array kit device of claim 2, wherein the oleaginous sealant has a specific gravity higher than a specific gravity of the liquid containing a biomolecule.

4. The array kit device of claim 3, wherein the plurality of wells includes at least one signal amplification well in each of the watertight portions such that the signal amplification well is configured to carry out a signal amplification reaction, and the signal amplification well is positioned such that the signal amplification well does not overlap with the injection ports and the discharge ports in a thickness direction of the base.

5. The array kit device of claim 1, wherein the base is made of a light transmissive material.

6. The array kit device of claim 1, wherein the base includes a substrate and a microporous array layer formed on the substrate such that the microporous array layer has a plurality of through holes forming the plurality of wells on the substrate and that the substrate is made of a light transmissive material.

7. The array kit device of claim 1, wherein the plurality of wells includes at least one signal amplification well in each of the watertight portions such that the signal amplification well is configured to carry out a signal amplification reaction, and the signal amplification well is positioned such that the signal amplification well does not overlap with the injection ports and the discharge ports in a thickness direction of the base.

8. The array kit device of claim 1, wherein the cover is formed such that the opening end of each of the discharge ports is positioned higher than a bottom surface of a respective one of the waste liquid vessels.

9. The array kit device of claim 1, wherein the cover is formed such that the plurality of waste liquid vessels is configured to hold the surplus amounts of the aqueous solution over the plurality of watertight portions in a thickness direction of the base and the cover.

10. A kit for analyzing a biomolecule, comprising:
the array kit device of claim 1;
a reagent for detecting the biomolecule; and
the oleaginous sealant deliverable from the injection ports into the watertight portions.

11. A kit for analyzing a biomolecule, comprising:
the array kit device of claim 2;
a reagent for detecting the biomolecule; and
the oleaginous sealant deliverable from the injection ports into the watertight portions,
wherein the aqueous solution is a buffer solution not containing a nucleic acid.

* * * * *